(12) United States Patent
Panja

(10) Patent No.: US 8,367,316 B2
(45) Date of Patent: Feb. 5, 2013

(54) HUMAN GASTROINTESTINAL STEM CELL-DERIVED PRIMARY INTESTINAL EPITHELIAL CELL SYSTEM AND METHODS OF USE THEREOF

(75) Inventor: Asit Panja, Somerset, NJ (US)

(73) Assignee: AlfaGene Bioscience, Inc., Fords, NJ (US)

( * ) Notice: Subject to any disclaimer, the term of this patent is extended or adjusted under 35 U.S.C. 154(b) by 244 days.

(21) Appl. No.: 12/772,949

(22) Filed: May 3, 2010

(65) Prior Publication Data

US 2010/0279275 A1 Nov. 4, 2010

Related U.S. Application Data

(60) Provisional application No. 61/174,609, filed on May 1, 2009.

(51) Int. Cl.
  *C12Q 1/70* (2006.01)
  *C12Q 1/02* (2006.01)
  *G01N 33/567* (2006.01)
  *C12N 5/071* (2010.01)

(52) U.S. Cl. ............. 435/5; 435/7.21; 435/29; 435/371

(58) Field of Classification Search ................... None
See application file for complete search history.

(56) References Cited

U.S. PATENT DOCUMENTS

| | | |
|---|---|---|
| 2003/0232074 A1 | 12/2003 | Lipford et al. |
| 2004/0132079 A1 | 7/2004 | Gupta et al. |
| 2005/0119273 A1 | 6/2005 | Lipford et al. |
| 2006/0058365 A1 | 3/2006 | Kohn et al. |
| 2006/0134128 A1 | 6/2006 | Seya et al. |
| 2007/0004654 A1 | 1/2007 | Raz et al. |
| 2009/0111746 A1 | 4/2009 | Platt et al. |
| 2009/0215908 A1 | 8/2009 | Upadhyay et al. |

FOREIGN PATENT DOCUMENTS

| | | |
|---|---|---|
| WO | 2004/053452 A2 | 6/2004 |
| WO | 2007/031879 A2 | 3/2007 |

OTHER PUBLICATIONS

Bocker et al (Int J Colorectal Dis. 2003; 18: 25-32).*
Panja (Lab Invest 2000; 80: 1473-1475).*
Spina et al. (Digestive and Liver Disease Supplements 1. 2007; 7-11).*
International Search Report and Written Opinion issued in PCT/US2010/033447, mailed Jan. 13, 2011.
MacKinnon et al., "Expression profile of toll-like receptors within the gastrointestinal tract of 2-day-old *Salmonella enteriditis*-infected broiler chickens," *Veterinary Microbiology*, 137:313-319 (2009).

\* cited by examiner

*Primary Examiner* — Scott Long
(74) *Attorney, Agent, or Firm* — Heslin Rothenberg Farley & Mesiti P.C.; Andrew K. Gonsalves

(57) ABSTRACT

The present invention relates to an intestinal primary epithelial cell system for detecting gastrointestinal segment-specific activation or suppression of a Toll-like receptor (TLR) by a target agent. The cell system includes an isolated human intestinal primary epithelial cell (HIPEC) line that expresses at least one TLR, where the HIPEC line is derived from a differentiable adult human gastrointestinal stem cell (ah-GISC) line. Also disclosed are various methods of using the cell system, a kit that includes the cell system, and an isolated cell culture including an isolated HIPEC line derived from a differentiable ahGISC line.

18 Claims, 19 Drawing Sheets

HUMAN GASTROINTESTINAL STEM CELL-DERIVED PRIMARY INTESTINAL EPITHELIAL CELL SYSTEM AND METHODS OF USE THEREOF

CROSS-REFERENCE TO RELATED APPLICATIONS

This application claims the benefit of U.S. Provisional Patent Application Ser. No. 61/174,609, filed May 1, 2009, which is hereby incorporated by reference in its entirety.

FIELD OF THE INVENTION

The present invention relates to an intestinal primary epithelial cell system that can be used, inter alia, for detecting gastrointestinal segment-specific activation or suppression of a Toll-like receptor (TLR) by a target agent. The present invention also relates to various methods of using the cell system.

BACKGROUND OF THE INVENTION

Toll-like receptors ("TLRs") are a class of proteins that play a role in the innate immune system. They are single membrane-spanning non-catalytic receptors that recognize structurally conserved molecules derived from microbes. Once these microbes have breached physical barriers such as the skin or intestinal tract mucosa, they are recognized by TLRs that then activate the immune cell responses.

TLRs are a type of pattern recognition receptor ("PRR") and recognize molecules that are broadly shared by pathogens but distinguishable from host molecules, collectively referred to as pathogen-associated molecular patterns (PAMPs). TLRs, together with the Interleukin-1 receptors, form a receptor superfamily known as the "Interleukin-1 Receptor/Toll-Like Receptor Superfamily"; all members of this family have in common a so-called TIR (Toll-IL-1 receptor) domain.

Three subgroups of TIR domains exist. Proteins with subgroup 1 TIR domains are receptors for interleukins that are produced by macrophages, monocytes and dendritic cells and all have extracellular Immunoglobulin (Ig) domains. Proteins with subgroup 2 TIR domains are classical TLRs, and bind directly or indirectly to molecules of microbial origin. A third subgroup of proteins containing TIR domains consists of adaptor proteins that are exclusively cytosolic and mediate signaling from proteins of subgroups 1 and 2.

TLRs are present in vertebrates, as well as in invertebrates. It is generally believed that most mammalian species have between ten and fifteen types of Toll-like receptors. Thirteen TLRs (named simply TLR1 to TLR13) have been identified in humans and mice together. It is generally believed that the endogenous activators of TLRs may participate in autoimmune diseases due to the sterotypic inflammatory response provoked by TLR activation. TLRs may be involved in the binding to host molecules including fibrinogen (involved in blood clotting) and heat shock proteins (HSPs) and host DNA.

TLRs are believed to function as dimers. Though most TLRs appear to function as homodimers, TLR2 forms heterodimers with TLR1 or TLR6, each dimer having different ligand specificity. TLRs also may depend on other co-receptors for full ligand sensitivity, such as in the case of TLR4's recognition of LPS, which requires MD-2. CD14 and Lipopolysaccharide Binding Protein (LBP) are known to facilitate the presentation of LPS to MD-2.

The adapter proteins and kinases that mediate TLR signaling have also been studied. Random germline mutagenesis with ENU has been used to study the TLR signaling pathways. When activated, it is believed that TLRs recruit adapter molecules within the cytoplasm of cells in order to propagate a signal. Four adapter molecules are known to be involved in signaling. These proteins are known as MyD88, Tirap (also called Mal), Trif, and Tram. The adapters may activate other molecules within the cell, including certain protein kinases (IRAK1, IRAK4, TBK1, and IKKi) that amplify the signal, and ultimately lead to the induction or suppression of genes that orchestrate the inflammatory response.

Toll-like receptors bind and become activated by different ligands, which, in turn are located on different types of organisms or structures. They also have different adapters to respond to activation and are located sometimes at the cell surface and sometimes to internal cell compartments. Furthermore, they are expressed by different types of leucocytes or other cell types (as shown in Table 1 below).

TABLE 1

| Receptor | Ligand(s) | Ligand Location | Adaptors | Location | Cell Types |
| --- | --- | --- | --- | --- | --- |
| TLR1 | multiple triacyl lipopeptides | bacteria | MyD88/ MAL | cell surface | monocytes/macrophages; a subset of dendritic cells; B lymphocytes |
| TLR2 | multiple glycolipids; multiple lipopeptides; multiple lipoproteins; lipteichoic acid; HSP70; zymosan | bacteria; host cells; fungi | MyD88/ MAL | cell surface | monocytes/macrophages; myeloid dendritic cells; mast cells |
| TLR3 | dsRNA; poly I:C | viruses | TRIF | cell compartment | dendritic cells; B lymphocytes |
| TLR4 | lipopolysaccharide; heat shock proteins; fibrinogen; heparan sulfate fragments; hyaluronic acid fragments | Gram-negative bacteria; host cells | MyD88; MAL; TRIF; TRAM | cell surface | monocytes/macrophages; myeloid dendritic cells; mast cells; intestinal epithelium |
| TLR5 | flagellin | bacteria | MyD88 | cell surface | monocytes/macrophages; a subset of dendritic cells; intestinal epithelium |

TABLE 1-continued

| Receptor | Ligand(s) | Ligand Location | Adaptors | Location | Cell Types |
|---|---|---|---|---|---|
| TLR6 | multiple diacyl lipopetides | mycoplasma | MyD88; MAL | cell surface | monocytes/macrophages; mast cells; B lymphocytes |
| TLR7 | imidazoquinoline; loxoribine; bropirimine; ssRNA | small synthetic compounds | MyD88 | cell surface | monocytes/macrophages; plasmacytoid dendritic cells; B lymphocytes |
| TLR8 | small synthetic compounds; ssRNA | | MyD88 | cell compartment | monocytes/macrophages; a subset of dendritic cells; mast cells |
| TLR9 | unmethylated CpG DNA | bacteria | MyD88 | cell compartment | monocytes/macrophages; plasmacytoid dendritic cells; B lymphocytes |
| TLR10 | *** | *** | *** | cell surface | monocytes/macrophages; B lymphocytes |
| TLR11 | profilm | Toxoplasma gondii | MyD88 | cell surface | monocytes/macrophages; liver cells; kidney; bladder epithelium |
| TLR12 | *** | *** | *** | *** | *** |
| TLR13 | *** | *** | *** | *** | *** |

Several reactions are possible following activation by ligands of microbial origin. Immune cells may produce signaling factors (cytokines) that trigger inflammation. For example, with a bacterial factor, the pathogen may be phagocytosed and digested, and its antigens presented to CD4+ T cells; with a viral factor, the infected cell may shut off its protein synthesis and may undergo programmed cell death (apoptosis). Immune cells that have detected a virus also may release anti-viral factors such as interferons.

There is a need for a cell system that can express TLRs and, therefore, be used to study gastrointestinal disorders in a gastrointestinal segment-specific manner.

SUMMARY OF THE INVENTION

According to one aspect, the present invention provides an intestinal primary epithelial cell system for detecting gastrointestinal segment-specific activation or suppression of a Toll-like receptor (TLR) by a target agent. The intestinal primary epithelial cell system includes an isolated human intestinal primary epithelial cell (HIPEC) line that expresses at least one TLR, where the HIPEC line is derived from a differentiable adult human gastrointestinal stem cell (ah-GISC) line.

According to another aspect, the present invention provides a method of detecting activation or suppression of a TLR in an epithelial cell system in response to a target agent. This method involves (i) providing an intestinal primary epithelial cell system of the present invention; (ii) contacting the intestinal primary epithelial cell system with a target agent; and (iii) subjecting the intestinal primary epithelial cell system to a TLR expression assay to determine a TLR expression profile of the cell system in response to the target agent, thereby determining whether the target agent activates, suppresses, or has no effect on TLR expression in the cell system.

According to another aspect, the present invention provides a method of screening a target agent for cytotoxicity. This method involves (i) providing an intestinal primary epithelial cell system of the present invention; (ii) contacting the cell system with a target agent; and (iii) subjecting the cell system to a cytoxicity assay under conditions effective to yield a toxicity profile of the target agent.

According to another aspect, the present invention provides a method of screening a target agent for permeability to a human epithelial cell. This method involves (i) providing an intestinal primary epithelial cell system of the present invention; (ii) contacting the cell system with a target agent; and (iii) subjecting the cell system to an epithelial cell permeability assay under conditions effective to yield a permeability profile of the target agent.

According to another aspect, the present invention provides a method of screening a target agent for immunostimulatory activity in a human epithelial cell. This method involves (i) providing an intestinal primary epithelial cell system of the present invention; (ii) contacting the cell system with a target agent; and (iii) subjecting the cell system to an immunostimultory assay to determine the immunostimulatory activity of the target agent on human epithelial cells.

According to another aspect, the present invention provides a method of identifying gastrointestinal segmental differential toxicity of a target agent. This method involves (i) providing a first intestinal primary epithelial cell system of the present invention, where the first cell system is derived from a first ahGISC line, and where the first ahGISC line is derived from a first human gastrointestinal segment; (ii) providing at least one test cell system that includes at least one test cell line; (iii) contacting the first cell system and the at least one test cell system with a target agent; (iv) subjecting the first cell system and the at least one test cell system to a cytoxicity assay under conditions effective to yield a toxicity profile of the target agent for the first cell system and the at least one test cell system; and (v) comparing the toxicity profiles of first cell system and the at least one test cell system to determine any differential toxicity of the first cell system and the at least one test cell system to the target agent.

According to another aspect, the present invention provides a method of determining gastrointestinal segmental bioavailability of a target agent. This method involves (i) providing a plurality of intestinal primary epithelial cell systems of the present invention, where each cell system corresponds to a different human gastrointestinal segment; (ii) contacting the plurality of cell systems with a target agent; (iii) subjecting the plurality of cell systems to a TLR expression assay to determine a TLR expression profile of each one of the cell systems in response to the target agent, thereby determining whether the target agent activates, suppresses, or has no effect on TLR expression in each one of the cell systems.

According to another aspect, the present invention provides a method of designing a drug for treating a gastrointesintal disorder. This method involves (i) providing an intestinal primary epithelial cell system of the present invention, where the cell system corresponds to particular human gastrointestinal segment; (ii) contacting the cell system with a target agent derived from a human gastrointestinal pathogen; (iii) subjecting the cell system to a blocking agent that binds to TLR; and (iv) assaying the cell system to determine whether the target agent is effective in inducing the TLR signaling pathway (see FIG. 13), where inducement of the TLR signaling pathway by the target agent indicates that a drug designed to target a signaling event in the TLR pathway will be effective, but that a drug designed to directly target TLR will not be effective against the human gastrointestinal pathogen.

According to another aspect, the present invention provides a kit for assaying functional response involving TLR signaling in a gastrointestinal segment-specific manner. The kit includes an intestinal primary epithelial cell system of the present invention; and a user manual that includes a TLR expression profile of the cell system.

According to another aspect, the present invention provides an isolated cell culture that includes an isolated HIPEC line derived from a differentiable ahGISC line.

As disclosed herein, the present invention provides a non-transformed human intestinal primary epithelial cell (HIPEC) system derived from human gastrointestinal stem cells. Because the HIPEC cell systems express TLRs and have unique TLR expression patterns, they are useful for a wide number of applications, particularly regarding drug discovery, toxicity assays of target drugs, TLR signaling pathway studies, drug-to-drug interaction studies, and many more uses as further described herein.

BRIEF DESCRIPTION OF THE DRAWINGS

The patent or application file may contain at least one drawing executed in color. Copies of this patent or patent application publication with color drawings, if any, will be provided by the U.S. Patent and Trademark Office upon request and payment of the necessary fee.

FIG. 8A: Microvilli (MV) are present on the apical surface of cells which contain large nuclei, bundles of microfilaments, and intercellular tight junction (TJ). FIG. 8B: Goblet cells are also present and are readily identified by their scant microvilli (M) and numerous mucin-containing vesicles (L).

FIG. 10A: Western blot analysis of lysates from HIPEC lines representing various segments of the intestine (MJR=rectum, JHS=sigmoid, TDT=transverse colon, AGA=ascending colon, BDJ jejunum, KPD=duodenum) using anti-β-catenin (upper panel) and anti-ZO-1 (lower panel) antibodies. HeLa (first lane—upper panel), a uterine-derived malignant epithelial cell line, served as a positive control for β-catenin, and HT29 (last lane—lower panel), a colonic adenocarcinoma epithelial cell line, served as a positive control for ZO-1. All HIPEC lines expressed both β-catenin and ZO-1 (β-catenin>>>ZO-1). FIG. 10B: Western blot analysis of lysates from one embodiment of HIPEC lines derived from a normal colon (WT) and small intestine (Jej) (BDJ) using an anti E-Cadherin monoclonal antibody. A lung tumor epithelial cell line A431 served as a positive control.

DETAILED DESCRIPTION OF THE INVENTION

Figure 1:
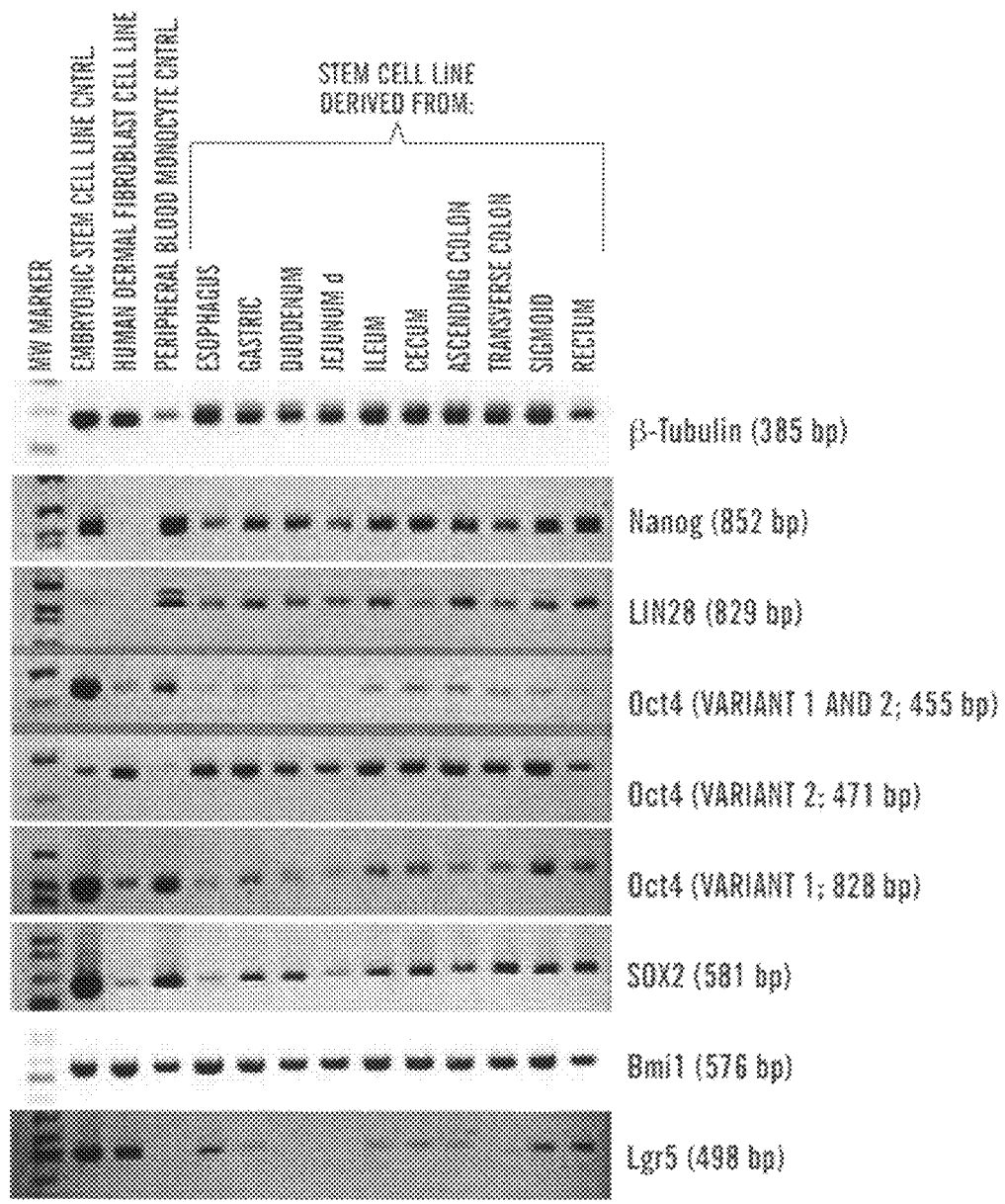
FIG. 1 shows the RT-PCR products from total RNA preparation of cell lines derived from the gastrointestinal tract. Lane: (1) molecular weight marker; (2) embryonic stem cell line control; (3) human dermal fibroblast cell line; (4) peripheral blood monocyte control; (5) esophagus derived stem cell line; (6) gastric derived stem cell line; (7) duodenum derived stem cell line; (8) jejunum derived stem cell line; (9) ileum derived stem cell line; (10) cecum derived stem cell line; (11) ascending colon derived stem cell line; (12) transverse colon derived stem cell line; (13) sigmoid derived stem cell line; and (14) rectum derived stem cell line.

The present invention provides, inter alia, homogenous non-transformed intestinal primary epithelial cell systems that express Toll-like receptors (TLRs) and that are derived from stem cells of the various segments (also referred to herein as regions) of the human gastrointestinal (GI) tract.

As discussed elsewhere herein, TLRs are transmembrane proteins that recognize pathogen associated molecular patterns (PAMPs) and activate the innate immune system against invading microbes. The cell systems of the present invention have been characterized in terms of their TLR expression profile, and also in terms of their response to immunostimulatory agents.

Therefore, the cell systems of the present invention are useful for a number of applications, including, without limitation, the following uses: (i) drug discovery (e.g., identification of drugs to treat various disorders and infections of the gastrointestinal tract or that involve the engagement of the TLR signaling pathway); (ii) preclinical drug studies (e.g., toxicity, permeability, biological action); (iii) drug-to-drug interaction studies; (iv) investigations of the etiology of GI disorders; and (v) drug design (e.g., identification and development of therapeutics against disorders and diseases that involve the TLR signaling pathway).

Another advantage of the cell systems of the present invention is that the cell systems are derived stem cells from each segment of the GI tract. Therefore, the cell systems of the present invention provide a cellular platform by which one can study GI immunostimulants, pathogens, and the like in a GI segment-specific manner.

As set forth below, the definitions of various terms relating to aspects of the present invention are provided.

The term "analyze" (or "analysis") as used herein refers to the process whereby a material is separated into constituent parts or elements or essential features. Analyses according to the described invention may be performed by numerous assays including, but not limited to, ELISA, HPLC, PCR, real-time PCR, permeability assays, immunochemistry, flow cytometry, TEER, SDS-PAGE, microscopic analysis, fluorescence microscopy, electron microscopy, NMR, LC-MS, or other analytical or bioanalytical assays known to artisans of skill in the art.

The term "antibody" as used herein refers to both polyclonal and monoclonal antibodies of any species. The ambit of the term encompasses not only intact immunoglobulin molecules, but also fragments and genetically engineered derivatives of immunoglobulin molecules and equivalent antigen binding molecules that retain the desired binding specificity.

The term "AUC" as used herein refers to the area under the plasma concentration-time curve for a single dose of a drug as described in Shargel and Yu, *Applied Biopharmaceutics and Pharmacokinetics*, 4th Edition, 1999, Appleton & Lange, Stamford, Conn., incorporated herein by reference. The AUC is proportional to the amount of drug that reaches the plasma.

The term "bioavailability" as used herein refers to the rate and extent to which an active or therapeutic ingredient of a therapeutic agent or drug is absorbed and becomes available at the site of drug action.

The terms "bio-similar matrix environment" and "BSME" are used interchangeably herein to refer to a growth substrate upon which human gastrointestinal epithelial stem-cell-like progenitor cells may be grown. A segment-specific BSME (herein referred to as "SS-BSME") is formed when each BSME is supplemented with gastrointestinal mucosal tissue derived growth supporting factors (MTD-GSF) appropriate for the isolated viable stem-cell-like progenitor cells of the gastrointestinal mucosal tissue segment of the human gastrointestinal tract that the BSME is to host. Thus, in some embodiments, stomach-BSME is supplemented with growth supporting factors derived from the mucosal tissues of the stomach. In some embodiments, duodenum-BSME is supplemented with growth supporting factors derived from the mucosal tissues of the duodenum. In some embodiments, jejunum-BSME is supplemented with growth supporting factors derived from the mucosal tissues of the jejunum. In some embodiments, ileum-BSME is supplemented with growth supporting factors derived from the mucosal tissues of the ileum. In some embodiments, colon-BSME is supplemented with growth supporting factors derived from the mucosal tissues of the colon. In some embodiments, rectum-BSME is supplemented with growth supporting factors derived from the mucosal tissues of the rectum. Each SS-BSME is adjusted to a pH most appropriate for the gastrointestinal epithelial stem-like epithelial progenitor cell it is to host. Thus, the stomach-BSME is adjusted to about pH 1.0 to about pH 2.0.

The duodenum-BSME is adjusted to about pH 4.0 to about pH 5.5. The jejunum-BSME is adjusted to about pH 5.5 to about pH 7.0. The ileum-BSME is adjusted to about pH 7.0 to about pH 7.5. The colon-BSME and rectum-BSME is adjusted to about pH 7.0 to about pH 7.5.

The term "chamber" as used herein refers to culture tubes, Petri dishes, microtiter plates, conical tubes, perfusion chambers, or any type of vessel useful in propagating and/or maintaining cells.

The term "crypt" as used herein refers to a pit-like depression or tubular recess. For example; within the gastrointestinal tract, at the base of the intestinal villi lie crypts where the epithelial cells proliferate.

The term "daughter cell" as used herein refers to one of the resultant cells that is generated when a cell undergoes cell division and divides into two cells. A cell that undergoes cell division and divides into two cells is referred to as a "parent" cell.

The term "differentiation" or "cellular differentiation" as used herein refers to the process by which a less specialized cell becomes a more specialized cell type. In adults, adult stem cells divide and create fully differentiated daughter cells during tissue repair and during normal cell turnover. Cell differentiation causes a cell's size, shape, polarity, metabolic activity, and responsiveness to signals to change dramatically. These changes largely are due to highly controlled modifications in gene expression. Cellular differentiation rarely involves a change in the DNA sequence itself; thus, different cells may have very different physical characteristics despite having the same genome. The term "differentiated" as used herein refers to having a different character or function from the surrounding structures or from the original type. The term "differentiable" as used herein refers to the ability to undergo differentiation or to become differentiated.

The term "disease" or "disorder" as used herein refers to an impairment of health or a condition of abnormal functions. The term "diseased state" as used herein refers to being in a condition of disease or disorder. The term "syndrome" as used herein refers to a pattern of symptoms indicative of some disease or condition. The term "condition" as used herein refers to a variety of health states and is meant to include disorders or disease caused by any underlying mechanism or disorder.

Diseases of the human gastrointestinal tract include, but are not limited to, achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis. Disease states often are quantified in the art using well known scoring systems, such as those elucidated in *Goodman & Gilman's The Pharmacological Basis of Therapeutics*, 10th Edition, Eds. I. G. Hardman and L. E. Limbird, McGraw-Hill Publishing, New York, N.Y., 2001, the entirety of which is incorporated herein by reference.

The term "dissolution" as used herein refers to the ability of a therapeutic agent to pass into a solution in a specific microenvironment determined by the highly interdependent influences of aqueous solubility, ionizability (pKa), and lipophilicity in the gastrointestinal environment. A "solution" generally is considered as a homogenous mixture of two or more substances. It is frequently, although not necessarily, a liquid. In a solution, the molecules of the solute (or dissolved substance) are uniformly distributed among those of the solvent.

The term "drug" as used herein refers to a therapeutic agent or any substance, other than food, used in the prevention, diagnosis, alleviation, treatment, or cure of disease. A drug is: (a) any article recognized in the official United States Pharmacopeia, official Homeopathic Pharmacopeia of the United States, or official National Formulary, or any supplement to any of them; (b) articles intended for use in the diagnosis, cure, mitigation, treatment, or prevention of disease in man or other animals; (c) articles (other than food) intended to affect the structure or any function of the body of man or other animals, and (d) articles intended for use as a component of any articles specified in (a), (b) or (c) above.

The term "efficacy" as used herein means a therapeutic agent's capacity to produce a therapeutically desired effect. Generally, a greater level of efficacy will be achieved by increasing the dose and/or frequency of administration of a therapeutic agent given to a population, such that a greater proportion of the population will receive a benefit and/or there will be a greater magnitude of benefit in an individual patient, or cell. If a first therapeutic agent is more potent than a second therapeutic agent, it will reach a greater level of efficacy than the second therapeutic agent using identical amounts of each.

The term human "gastrointestinal epithelial stem cell-like progenitor cell" as used herein refers to a cell having the phenotype cytokeratin(+),$\beta$-1-integrin(+), defensin-5(+), trefoil factor-3(+), mucin-2(+), chomogranin-A(+), intestinal alkaline phosphatase(+), lysozyme(+) or at least $\beta$-1-integrin $^{(+)}$, and cytokeratin$^{(+)}$.

The term "gastrointestinal mucosal tissue segments" as used herein refers to isolated anatomical segments of the human gastrointestinal tract. Gastrointestinal mucosal tissue segments include those prepared from the stomach, the duodenum, the jejunum, the ileum, the ascending colon, the transverse colon, the sigmoid, and the rectum.

The term "HIPEC" as used herein refers to human intestinal primary epithelial cell lines derived from gastrointestinal epithelial stem cell-like progenitor cells according to the disclosed methods. The term "HGISC" as used herein refers to human gastrointestinal stem cells.

The term "human gastrointestinal tract" as used herein refers to the coordinated structure having the function of ingesting and absorbing nutrients and excreting unabsorbed and waste products.

As used herein the term "inflammation" refers to a physiologic response to infection and injury in which cells involved in detoxification and repair are mobilized to the compromised site by inflammatory mediators. The classic signs of inflammation are pain (dolor), heat (calor), redness (rubor), swelling (tumor), and loss of function (functio laesa). Histologically, inflammation involves a complex series of events, including dilatation of arterioles, capillaries, and venules, with increased permeability and blood flow; exudation of fluids, including plasma proteins; and leukocytic migration into the inflammatory focus.

The term "acute inflammation" as used herein, refers to inflammation, usually of sudden onset, characterized by the classical signs, with predominance of the vascular and exudative processes. The term "chronic inflammation" as used herein refers to inflammation of slow progress and marked chiefly by the formation of new connective tissue; it may be a continuation of an acute form or a prolonged low-grade form, and usually causes permanent tissue damage.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The term "inflammatory mediators" as used herein refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-8, tumor necrosis factor (TNF), interferon-gamma, and interleukin 12.

The term "mucosa" as used herein refers to the mucous tissue lining various tubular structures, which comprises an epithelium, a lamina propria, and in the digestive tract, a layer of smooth muscle (muscularis mucomucosa).

The term "mucosal" as used herein means relating to the mucosa or mucous membrane.

The term "native" as used herein refers to the condition of an organ, molecule, compound, protein, or nucleic acid as it would normally occur in nature. For example, a native human gastrointestinal tract refers to a gastrointestinal tract found within a normal human subject.

The term "oral bioavailability" as used herein refers to the fraction of a drug dose given orally that is absorbed into the plasma after a single administration to a subject. A preferred method for determining the oral bioavailability is by dividing the AUC of a drug dose given orally by the AUC of the same drug dose given intravenously to the same patient, and expressing the ratio as a percent. Other methods for calculating oral bioavailability will be familiar to those skilled in the art, and are described in greater detail in Shargel and Yu, *Applied Biopharmaceutics and Pharmacokinetics,* 4th Edition, 1999, Appleton & Lange, Stamford, Conn., incorporated herein by reference.

The term "permeability" as used herein means the property of being permeable.

The term "permeable" as used herein means permitting the passage of substances (e.g., liquids, gases, heat, etc.), as through a membrane or other structure.

The term "progenitor cell" as used herein refers to an immature or undifferentiated cell population. Progenitor cells have a capacity for self-renewal and differentiation, although these properties may be limited. The majority of progenitor cells lie dormant or possess little activity in the tissue in which they reside. They exhibit slow growth and their main role is to replace cells lost by normal attrition. Upon tissue damage or injury, progenitor cells can be activated by growth factors or cytokines, leading to increased cell division important for the repair process.

The term "regional specificity" as used herein refers to the ability of a therapeutic agent to affect a specific identified segment of the human gastrointestinal tract.

The term "specificity" as used herein refers to the ability of a biological molecule to selectively affect a target substance and to not affect other substances commonly recognized by nonselective biological molecules of a similar type; for example, an antibody that binds to an antigen.

The term "stem cell" as used herein refers to undifferentiated cells having high proliferative potential with the ability to self-renew that can generate daughter cells that can undergo terminal differentiation into more than one distinct cell type. A cell that is able to differentiate into many cell types may be referred to as "pluripotent." A cell that is able to differentiate into all cell types may be referred to as "totipotent." Pluripotent stem cells undergo further specialization into multipotent progenitor cells that then give rise to functional cells. Examples of stem and progenitor cells include, but are not limited to: hematopoietic stem cells (adult stem cells) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; and muscle satellite cells (progenitor cells) that contribute to differentiated muscle tissue.

The term "therapeutic agent" as used herein refers to a drug, molecule, nucleic acid, protein, composition or other substance that provides a therapeutic effect.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$ which describes the dose in a particular dosage that is therapeutically effective for a particular disease manifestation in 50% of a population.

The term "therapeutic effect" as used herein refers to a consequence of treatment, the results of which are judged to be desirable and beneficial. For example, a therapeutic effect may include, directly or indirectly, the arrest, reduction, or elimination of a disease manifestation. A therapeutic effect may also include, directly or indirectly, the arrest, reduction or elimination of the progression of a disease manifestation. A therapeutic effect may directly or indirectly kill the diseased cells, arrest the accumulation of diseased cells, or reduce the accumulation of diseased cells in a human subject with a disease such as, but not limited to, achalasia, Barrett's esophagus, colorectal cancer, gastric cancer, esophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux esophagitis, and ulcerative colitis.

The terms "therapeutically effective amount" and "pharmaceutically effective amount" are used interchangeably to refer to the amount that results in a therapeutic beneficial effect. The term as used herein also refers to the dosage of a therapeutic agent that directly or indirectly reduces or increases the activity of molecules secreted by diseased and/or non-diseased cells participating in a disease manifestation, such that the amount of therapeutic agent arrests, reduces, or eliminates altogether the degree of the disease manifestation. Typically, a therapeutically effective amount will also eliminate, reduce, or prevent the progression of one or more diseases. A skilled artisan recognizes that in many cases a therapeutic agent may not provide a cure, but may provide only a partial benefit. Furthermore, the skilled artisan recognizes that because individual patients and disease states may vary, some patients may receive little or no benefit at all. A dosage of therapeutic agent that "kills," "arrests," "reduces," or "eliminates" as described above, in at least some patients, is considered therapeutically effective. The term "dosage" as used herein refers to the dose or amount, and frequency of administering of a therapeutic agent in prescribed amounts and frequency. The term "dose" as used herein refers to the amount of therapeutic agent to be taken or applied all at one time or in fractional amounts within a given period.

The term "therapeutic target" as used herein refers to a native protein, molecule, compound, nucleic acid, organ, gland, ligand, receptor, organelle, or cell whose activity is modified by a drug resulting in a desirable therapeutic effect.

The term "trans-epithelial electrical resistance" ("TEER") as used herein refers to a functional assay that detects nanoscale alterations of an epithelial test barrier.

The term "transport" as used herein refers to the movement or transference of biochemical substances in biologic systems. "Active transport" refers to the passage of ions or molecules across a cell membrane, not by passive diffusion, but by an energy-consuming process at the expense of catabolic processes proceeding within the cell; in active transport, movement takes place against an electrochemical gradient. "Facilitated (or passive) transport" refers to the protein-mediated transport of a compound across a biomembrane that is not ion-driven and is saturable. "Paracellular transport" refers to solvent movement across an epithelial cell layer through the tight junctions between cells. "Transcellular transport" refers to transport of macromolecules across a cell, including transport through channels, pumps, and transporters, as well as transcytosis (endocytosis of macromolecule at one side of a monolayer and exocytosis at the other side).

As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, and protecting from harmful or annoying stimuli.

The term "toxicity" as used herein refers to any undesired harmful effect of a therapeutic agent. A therapeutic agent is said to be toxic or have toxicity if it causes a toxicity manifestation in a percentage of a population.

The term "villi" as used herein refers to projections from the surface, especially of a mucous membrane. In nature, intestinal villi are projections, about 0.5 mm to about 1.5 mm in length, of the mucous membrane of the small intestine. They are leaf-shaped in the duodenum and become shorter, more finger-shaped, and sparser in the ileum.

Provided herein below are various aspects of the present invention. Suitable materials and methods relating to aspects of producing the ahGISC lines and HIPEC lines of the present invention are described by applicant in its published patent applications US-2009/0269769 and/or US-2010/0093552, the entire disclosures of which are hereby incorporated by reference herein.

According to one aspect, the present invention provides an intestinal primary epithelial cell system for detecting gastrointestinal segment-specific activation or suppression of a Toll-like receptor (TLR) by a target agent. The intestinal primary epithelial cell system includes an isolated human intestinal primary epithelial cell (HIPEC) line that expresses at least one TLR, where the HIPEC line is derived from a differentiable adult human gastrointestinal stem cell (ahGISC) line.

In one embodiment of the cell system of the present invention, the HIPEC line expresses one or multiple TLRs such as: TLR1, TLR2, TLR3, TLR4, TLR5, TLR6, TLR7, TLR8, TLR9, TLR10, TLR11, TLR12, and TLR13.

In another embodiment of the cell system of the present invention, the HIPEC line has a TLR expression profile that corresponds to a particular mature cell phenotype, including, without limitation, mature cell phenotypes such as: a columnar epithelial cell, a Paneth cell, a Goblet cell, an enteroendocrine chromaffin cell, a neuronal cell type, and a mesenchymal cell.

In another embodiment of the cell system of the present invention, the ahGISC line is derived from at least one human gastrointestinal segment. Suitable human gastrointestinal segments can include, without limitation, an esophagus segment, a stomach segment, a jejunum segment, an ileum segment, a duodenum segment, a cecum segment, an appendix segment, an ascending colon segment, a transverse colon segment, a descending colon segment, a sigmoid colon segment, and a rectum segment.

In another embodiment of the cell system of the present invention, the HIPEC line can include cells having a mature cell phenotype such as a columnar epithelial cell, a Paneth cell, a Goblet cell, an enteroendocrine chromaffin cell, a neuronal cell type, and a mesenchymal cell.

In another embodiment of the cell system of the present invention, the ahGISC line can include cells expressing at least one stem cell biomarker. Suitable stem cell biomarkers are well known in the art. Particular stem cell biomarkers can include, without limitation, Nanog, LIN28, Oct4, SOX2, Bmi-1, and Lgr5.

In another embodiment of the cell system of the present invention, the ahGISC line can include cells having at least a $\beta$-1-integrin$^{(+)}$cytokeratin$^{(+)}$ phenotype. In another embodiment, the ahGISC line can include cells having a phenotype of cytokeratin(+), 1integrin(+), defensin-5(+), trefoil factor-3 (+), mucin-2(+), chomogranin-A(+), intestinal alkaline phosphatase(+), lysozyme(+).

In another embodiment of the cell system of the present invention, the target agent binds to at least one TLR, is an activator of at least one TLR, is an enhancer of at least one TLR, inhibits at least one TLR, is an agonist of at least one TLR, or is an antagonist of at least one TLR.

In another embodiment of the cell system of the present invention, the target agent is derived from a human pathogen. The human pathogen can be from any classification, including, for example, a virus, a bacterium, a fungus, a parasite, and a protozoan.

In another embodiment of the cell system of the present invention, the target agent is a therapeutic agent for treating a disorder that alters TLR expression on intestinal epithelial cells and/or mediated signals, including disorders such as autoimmunity disorders, bacterial infections, viral infections, parasite infections, protozoan infections, fungal infections, fungal-associated disorders, basal cell carcinoma, herpes simplex virus (HSV-1), encephalitis (HSE), human primary immunodeficiency, and the like.

The cell system of the present invention can be applied to various uses, some of which are further described below.

In one embodiment of the cell system of the present invention, the cell system is used to assess a bioactivity parameter of the target agent. Various bioactivity parameters are well known to those of ordinary skill in the art. However, certain of the bioactivity parameters can include, without limitation, immunostimulatory activity, permeability, absorption, uptake, cellular toxicity, transepithelial electrical resistance, and cytokine production.

In another embodiment of the cell system of the present invention, the cell system is used (i) to analyze gastrointestinal epithelium, (ii) to study the etiology of gastrointestinal disorders, and/or (iii) to identify therapeutics effective to treat gastrointestinal disorders.

As contemplated by the present invention, gastrointestinal disorders can include, without limitation, such disorders as the following: achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis.

In another embodiment of the cell system of the present invention, the cell system is used to determine whether the gastrointestinal disorder develops by way of a TLR-mediated mechanism in a gastrointestinal segment-specific manner.

In another embodiment of the cell system of the present invention, the cell system is used to determine segmental bioavailability of a target agent.

In another embodiment of the cell system of the present invention, the cell system is used to identify a stem cell marker profile specific to a segment of the gastrointestinal tract.

In another embodiment of the cell system of the present invention, the target agent is an immunostimulatory agent. Suitable immunostimulatory agents are well known in the art and can include, without limitation, the following: lipopolysaccharide (LPS), an interferon (IFN) such as IFN-α, IFN-β, IFN-γ, and IFN-ω, an interleukin (IL) such IL-1β, IL-8, and IL-18, a cytokine such as tumor necrosis factor alpha (TNFα), a synthetic lipoprotein such as Pam3CSK4, Flagellin, and the like.

According to another aspect, the present invention provides a method of detecting activation or suppression of a TLR in an epithelial cell system in response to a target agent. This method involves (i) providing an intestinal primary epithelial cell system of the present invention; (ii) contacting the intestinal primary epithelial cell system with a target agent; and (iii) subjecting the intestinal primary epithelial cell system to a TLR expression assay to determine a TLR expression profile of the cell system in response to the target agent, thereby determining whether the target agent activates, suppresses, or has no effect on TLR expression in the cell system.

In one embodiment of the above method of the present invention, the TLR expression assay is effective to determine whether the cell system's response to the target agent is due to a direct or indirect interaction between the target agent and TLR.

In another embodiment of the above method of the present invention, the target agent binds to at least one TLR, is an activator of at least one TLR, is an enhancer of at least one TLR, inhibits at least one TLR, is an agonist of at least one TLR, or is an antagonist of at least one TLR.

In another embodiment of the above method of the present invention, the target agent is a therapeutic agent for treating a disorder that alters TLR expression on intestinal epithelial cells and/or mediated signals. Such disorders can include, without limitation, autoimmunity disorders, bacterial infections, viral infections, parasite infections, protozoan infections, fungal infections, fungal-associated disorders, basal cell carcinoma, herpes simplex virus (HSV-1), encephalitis (HSE), human primary immunodeficiency, and the like.

In another embodiment of the above method of the present invention, the target agent is an immunostimulatory agent.

In another embodiment of the above method of the present invention, the target agent is derived from a human pathogen, where the human pathogen can be a virus, a bacterium, a fungus, a parasite, and a protozoan. The target agent derived from a human pathogen can be of various types of agents, including, without limitation, a compound, a nucleic acid molecule, a peptide, an enzyme, a biomarker, a toxin, and the like. However, any agent or biomarker corresponding to the human pathogen of interest is contemplated by the present invention.

In another embodiment of the above method of the present invention, the target agent is subject to screening for use as a therapeutic effective to a treat gastrointestinal disorder. Such gastrointestinal disorders can include, for example, achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis.

According to another aspect, the present invention provides a method of screening a target agent for cytotoxicity. This method involves (i) providing an intestinal primary epithelial cell system of the present invention; (ii) contacting the cell system with a target agent; and (iii) subjecting the cell system to a cytoxicity assay under conditions effective to yield a toxicity profile of the target agent.

Various cytotoxicity assays (also referred to herein as toxicity assays) are well known in the art. One such assay includes the MTT cytotoxicity assay. However, the present invention is not meant to be limited to a particular cytotoxicity assay.

According to another aspect, the present invention provides a method of screening a target agent for permeability to a human epithelial cell. This method involves (i) providing an intestinal primary epithelial cell system of the present invention; (ii) contacting the cell system with a target agent; and (iii) subjecting the cell system to an epithelial cell permeability assay under conditions effective to yield a permeability profile of the target agent.

In one embodiment of the above method of the present invention, the cell system is provided in the form of a cell monolayer. Various methods of forming a monlayer are known in the art, and more particularly are described by applicant in its published patent applications US-2009/0269769 and/or US-2010/0093552, the entire disclosures of which are hereby incorporated by reference herein.

According to another aspect, the present invention provides a method of screening a target agent for immunostimulatory activity in a human epithelial cell. This method involves (i) providing an intestinal primary epithelial cell system of the present invention; (ii) contacting the cell system with a target agent; and (iii) subjecting the cell system to an immunostimultory assay to determine the immunostimulatory activity of the target agent on human epithelial cells.

In one embodiment of the above method of the present invention, the immunostimulatory assay can include using known immunostimulatory agents as controls. Suitable immunostimulatory agents are well known in the art and can include, without limitation, the following: lipopolysaccharide (LPS), an interferon (IFN) such as IFN-α, IFN-β, IFN-γ, and IFN-ω, an interleukin (IL) such IL-1β, IL-8, and IL-18, a cytokine such as tumor necrosis factor alpha (TNFα), a synthetic lipoprotein such as Pam3CSK4, Flagellin, and the like.

In another embodiment of the above method of the present invention, the immunostimulatory assay can include measuring nitric oxide (NO) production in the cell system to determine the immunostimulatory activity of the target agent. Those of ordinary skill in the art will readily understand how NO production can be used to determine the immunostimulatory activity of a target agent, and how such knowledge can be used to study and develop potential therapeutics against GI tract disorders.

According to another aspect, the present invention provides a method of identifying gastrointestinal segmental differential toxicity of a target agent. This method involves (i) providing a first intestinal primary epithelial cell system of the present invention, where the first cell system is derived from a first ahGISC line, and where the first ahGISC line is derived from a first human gastrointestinal segment; (ii) providing at least one test cell system that includes at least one test cell line; (iii) contacting the first cell system and the at least one test cell system with a target agent; (iv) subjecting the first cell system and the at least one test cell system to a cytoxicity assay under conditions effective to yield a toxicity profile of the target agent for the first cell system and the at least one test cell system; and (v) comparing the toxicity profiles of first cell system and the at least one test cell system to determine any differential toxicity of the first cell system and the at least one test cell system to the target agent.

In one embodiment of the above method of the present invention, the first ahGISC line is derived from a first human gastrointestinal segment. Suitable GI segments can include, for example, an esophagus segment, a stomach segment, a jejunum segment, an ileum segment, a duodenum segment, a cecum segment, an appendix segment, an ascending colon segment, a transverse colon segment, a descending colon segment, a sigmoid colon segment, and a rectum segment.

In another embodiment of the above method of the present invention, the at least one test cell system can be a second cell system of the present invention. In this embodiment, the second cell system is derived from a second ahGISC line, where the second ahGISC line is derived from a second human gastrointestinal segment that is different from the first human gastrointestinal segment.

In another embodiment of the above method of the present invention, the second ahGISC line is derived from a second human gastrointestinal segment such as an esophagus segment, a stomach segment, a jejunum segment, an ileum segment, a duodenum segment, a cecum segment, an appendix segment, an ascending colon segment, a transverse colon segment, a descending colon segment, a sigmoid colon segment, and a rectum segment.

In another embodiment of the above method of the present invention, the HIPEC line can include cells having a mature cell phenotype such as a columnar epithelial cell, a Paneth cell, a Goblet cell, an enteroendocrine chromaffin cell, a neuronal cell type, and a mesenchymal cell.

In another embodiment of the above method of the present invention, the at least one test cell line can be a carcinoma cell line. Suitable carcinoma cell lines are well known to those of ordinary skill in the art.

According to another aspect, the present invention provides a method of determining gastrointestinal segmental bioavailability of a target agent. This method involves (i) providing a plurality of intestinal primary epithelial cell systems of the present invention, where each cell system corresponds to a different human gastrointestinal segment; (ii) contacting the plurality of cell systems with a target agent; (iii) subjecting the plurality of cell systems to a TLR expression assay to determine a TLR expression profile of each one of the cell systems in response to the target agent, thereby determining whether the target agent activates, suppresses, or has no effect on TLR expression in each one of the cell systems.

In one embodiment of the above method of the present invention, the different human gastrointestinal segments can be of an esophagus segment, a stomach segment, a jejunum segment, an ileum segment, a duodenum segment, a cecum segment, an appendix segment, an ascending colon segment, a transverse colon segment, a descending colon segment, a sigmoid colon segment, or a rectum segment.

In another embodiment of the above method of the present invention, the HIPEC line can include cells having a mature cell phenotype such as a columnar epithelial cell, a Paneth cell, a Goblet cell, an enteroendocrine chromaffin cell, a neuronal cell type, and a mesenchymal cell.

According to another aspect, the present invention provides a method of designing a drug for treating a gastrointestinal disorder. This method involves (i) providing an intestinal primary epithelial cell system of the present invention, where the cell system corresponds to particular human gastrointestinal segment; (ii) contacting the cell system with a target agent derived from a human gastrointestinal pathogen; (iii) subjecting the cell system to a blocking agent that binds to TLR; and (iv) assaying the cell system to determine whether the target agent is effective in inducing the TLR signaling pathway, where inducement of the TLR signaling pathway by the target agent indicates that a drug designed to target a signaling event in the TLR pathway will be effective, but that a drug designed to directly target TLR will not be effective against the human gastrointestinal pathogen.

In one embodiment of the above method of the present invention, the human gastrointestinal pathogen can include, without limitation, a virus, a bacterium, a fungus, a parasite, or a protozoan. Further, as discussed herein above with respect to other aspects of the present invention, the target agent derived from the human gastrointestinal pathogen can be of various a types of agent, including, for example, a compound, a nucleic acid molecule, a peptide, an enzyme, a biomarker, a toxin, and the like.

According to another aspect, the present invention provides a kit for assaying functional response involving TLR signaling in a gastrointestinal segment-specific manner. The kit includes an intestinal primary epithelial cell system of the present invention; and a user manual that includes a TLR expression profile of the cell system.

According to another aspect, the present invention provides an isolated cell culture that includes an isolated HIPEC line derived from a differentiable ahGISC line.

Various other aspects of the present invention are further described herein below.

The present invention provides a system for drug discovery utilizing epithelial stem cells isolated from at least one segment of the human gastrointestinal tract and/or primary non-transformed epithelial cell lineages derived from cultured epithelial stem cells. The epithelial stem cells isolated from at least one segment of the human gastrointestinal tract and/or primary non-transformed epithelial cell lineages derived from cultured epithelial stem cells may express at least one TLR. The present invention further provides a system that further comprises methods for the analysis of TLR expression. The demonstrated differential expression profile of TLRs in non-transformed primary epithelial cells from each region of the GI tract as described in the invention facilitates studies and understanding of region/site (e.g. small intestine vs. large intestine and/or upper GI tract vs. lower GI tract, or jejunum vs. ileum in the small intestine, cecum vs. rectum in the large intestine etc.) specific mechanisms of interactions of various types invading pathogens with the GI epithelial cells.

The present invention further provides a system that allows identification of altered TLR expression on intestinal epithelial cells and/or mediated signals causing aberrant immunity, infection, inflammation and/or malignant transformation in the GI tract. Such information may allow development of site specific therapeutic development including vaccines for TLR mediated pathological conditions.

The present invention further provides a system that further comprises a cellular platform of human GISC derived non-transformed primary epithelial cells from each segment of the GI tract that serves as a unique tool for in vitro studies of region/site specific invasion/adhesion assay for gastrointestinal infectious agents (e.g. salmonella, shigella, enterotoxic E-coli).

The present invention further provides a system that further allows identification of altered TLR expression on intestinal epithelial cells and/or mediated signals related to autoimmunity disorders, fungal infections or fungal-associated disorders, such as, but not limited to, aspergillosis, basal cell carcinoma, herpes simplex virus, (HSV-1), encephalitis (HSE), and human primary immunodeficiency.

According to one aspect, the present invention provides a system to determine the segmental bioavailability of a therapeutic agent comprising differentiable gastrointestinal segment-specific human epithelial stem-cell-like progenitor cells isolated from at least one human mucosal tissue derived from at least one human gastrointestinal segment, wherein the cells may express at least one toll-like receptor protein.

According to one embodiment, the therapeutic agent binds to at least one TLR. According to another embodiment, the therapeutic agent is an activator of at least one TLR. According to another embodiment, the therapeutic agent is an enhancer of at least one TLR. According to another embodiment, the therapeutic agent inhibits at least one TLR. According to another embodiment, the therapeutic agent is an agonist of at least one TLR. According to another embodiment, the therapeutic agent is an antagonist of at least one TLR.

According to one embodiment, the gastrointestinal segment-specific human epithelial stem cell-like progenitor cells are cultivated on a bio-similar matrix environment formed from the human mucosal tissue derived from the human gastrointestinal segment. According to another embodiment, the segment is a stomach segment. According to another embodiment, the segment is a jejunum segment. According to another embodiment, the segment is an ileum segment. According to another embodiment, the segment is a duodenum segment. According to another embodiment, the segment is an ascending colon segment. According to another embodiment, the segment is a transverse colon segment. According to another embodiment, the segment is a sigmoid colon segment. According to another embodiment, the segment is a rectum segment.

According to another embodiment, the differentiable gastrointestinal segment-specific human epithelial stem-cell-like progenitor cell optionally differentiates into a mature cell phenotype. According to another embodiment, the mature cell phenotype is a columnar epithelial cell. According to another embodiment, the mature cell phenotype is a Paneth cell. According to another embodiment, the mature cell phenotype is a goblet cell. According to another embodiment, the mature cell phenotype is an enteroendocrine chromaffin cell. According to another embodiment, the mature cell phenotype is a neuronal cell type.

According to another embodiment, the differentiable gastrointestinal segment-specific human epithelial stem-cell-like progenitor cell is a mesenchymal cell.

According to another embodiment, the system is used to assess at least one parameter of permeability of the therapeutic agent. According to another embodiment, the system is used to assess absorption of the therapeutic agent. According to another embodiment, the system is used to assess uptake of the therapeutic agent. According to another embodiment, the system is used to assess cellular toxicity of the therapeutic agent. According to another embodiment, the system is used to assess transepithelial electrical resistance.

According to another embodiment, the differentiable gastrointestinal segment-specific human stem epithelial cell-like progenitor cells on the at least one bio-similar matrix environment are used to determine variations in DNA and/or RNA characteristics produced in response to the therapeutic agent.

According to another embodiment, the system is used to determine segment-specific metabolic byproducts of the therapeutic agent.

According to another embodiment, the bio-similar matrix environment formed from the at least one mucosal tissue derived from the stomach is serially connected to the bio-similar matrix environment formed from the at least one mucosal tissue derived from the jejunum, which is serially connected to the bio-similar matrix environment formed from the at least one mucosal tissue derived from the ileum, which is serially connected to the bio-similar matrix environment formed from the at least one mucosal tissue derived from the duodenum, which is serially connected to the bio-similar matrix environment formed from the at least one mucosal tissue derived from the ascending colon segment, which is serially connected to the bio-similar matrix environment formed from the at least one mucosal tissue derived from the transverse colon segment, which is serially connected to the bio-similar matrix environment formed from the at least one mucosal tissue derived from the sigmoid colon segment, which is serially connected to the bio-similar matrix environment formed from the at least one mucosal tissue derived from the rectum to form an in vitro model of the human gastrointestinal tract According to another embodiment, the differentiable gastrointestinal segment-specific human epithelial stem cell-like progenitor cell has at least a $\beta$-1-integrin$^{(+)}$ cytokeratin$^{(+)}$ phenotype. According to another embodiment, the differentiable gastrointestinal segment-specific human epithelial stem cell-like progenitor cell has a phenotype of cytokeratin (+), 0-1-integrin(+), defensin-5(+), trefoil factor-3(+), mucin-2(+), chomogranin-A(+), intestinal alkaline phosphatase(+), lysozyme(+).

According to another aspect, the present invention provides a method to determine gastrointestinal segmental effectiveness of a therapeutic agent, the method comprising the steps: (a) isolating differentiable gastrointestinal segment-specific human epithelial stem-cell-like progenitor cells from at least one mucosal tissue derived from at least one human gastrointestinal segment; (b) cultivating the differentiable gastrointestinal segment-specific human epithelial stem cell-like progenitor cells on at least one bio-similar matrix environment formed from the at least one mucosal tissue derived from the at least one human gastrointestinal segment; (c) exposing the differentiable gastrointestinal segment-specific human epithelial stem cell-like progenitor cells on the at least one bio-similar matrix environment to the therapeutic agent; and (d) analyzing the differentiable gastrointestinal segment-specific human epithelial stem cell-like progenitor cells to determine regional specificity of the therapeutic agent;

wherein the cells of step (a), step (b), step (c) and/or step (d) may express at least one TLR.

According to one embodiment, the therapeutic agent binds to at least one TLR. According to another embodiment, the therapeutic agent is an activator of at least one TLR. According to another embodiment, the therapeutic agent is an enhancer of at least one TLR. According to another embodiment, the therapeutic agent inhibits at least one TLR. According to another embodiment, the therapeutic agent is an agonist of at least one TLR. According to another embodiment, the therapeutic agent is an antagonist of at least one TLR.

According to one embodiment, a first human gastrointestinal segment is a stomach segment. According to another embodiment, a first human gastrointestinal segment is a jejunum segment. According to another embodiment, a first human gastrointestinal segment is an ileum segment. According to another embodiment, a first human gastrointestinal segment is a duodenum segment. According to another embodiment, a first human gastrointestinal segment is an ascending colon segment. According to another embodiment, a first human gastrointestinal segment is a transverse colon segment. According to another embodiment, a first human gastrointestinal segment is a sigmoid colon segment. According to another embodiment, a first human gastrointestinal segment is a rectum segment.

According to another embodiment, the differentiable gastrointestinal segment-specific human epithelial stem cell-like progenitor cells on the at least one bio-similar matrix environment are used to determine variations in DNA and/or RNA characteristics produced in response to the therapeutic agent.

According to another embodiment, the method further comprises the step of serially connecting the bio-similar matrix environment formed from the at least one mucosal tissue derived from the stomach segment to the bio-similar matrix environment formed from the at least one mucosal tissue derived from the jejunum segment to the bio-similar matrix environment formed from the at least mucosal tissue derived from the ileum segment, to the bio-similar matrix environment formed from the at least one mucosal tissue derived from the duodenum segment to the bio-similar matrix environment formed from the at least one mucosal tissue derived from the ascending colon segment to the bio-similar matrix environment formed from the at least one mucosal tissue derived from the transverse colon segment to the bio-similar matrix environment formed from the at least one mucosal tissue derived from the sigmoid colon segment to the bio-similar matrix environment formed from the at least one mucosal tissue derived from the rectum to form an in vitro model of the human gastrointestinal tract.

According to another embodiment, the differentiable gastrointestinal segment-specific human epithelial stem cell-like progenitor cell has at least a $\beta$-1-integrin$^{(+)}$ cytokeratin$^{(+)}$ phenotype. According to another embodiment, the differentiable gastrointestinal segment-specific human stem epithelial cell-like progenitor cell has a phenotype of cytokeratin (+), $\beta$-1integrin(+), defensin-5(+), trefoil factor-3(+), mucin-2(+), chomogranin-A(+), intestinal alkaline phosphatase(+), lysozyme(+).

According to another embodiment, the therapeutic agent is for treating a disorder related to altered TLR expression on intestinal epithelial cells and/or mediated signals. These disorders may include, but are not limited to, those of autoimmunity disorders, fungal infections or fungal-associated disorders, such as, but not limited to, aspergillosis, basal cell carcinoma, herpes simplex virus, (HSV-1), encephalitis (HSE), and human primary immunodeficiency.

According to another aspect, the present invention provides a method to identify therapeutic targets useful in treating inflammatory diseases of the gastrointestinal tract, the method comprising the steps: (a) isolating differentiable gastrointestinal segment-specific human epithelial stem-cell-like progenitor cells from at least one human mucosal tissue derived from at least one human gastrointestinal segment; (b) cultivating the differentiable gastrointestinal segment-specific human epithelial stem cell-like progenitor cells on at least one bio-similar matrix environment formed from the at least one human mucosal tissue derived from the at least one human gastrointestinal segment; (c) exposing the differentiable gastrointestinal segment-specific human epithelial stem cell-like progenitor cells on the at least one bio-similar matrix environment to a therapeutic agent; (d) analyzing the differentiable gastrointestinal segment-specific human epithelial stem cell-like progenitor cells on the at least one bio-similar matrix environment exposed to the therapeutic agent to identify at least one marker as a therapeutic target; wherein the cells of step (a), step (b), step (c) and/or step (d) may express at least one TLR.

According to one embodiment, the therapeutic agent binds to at least one TLR. According to another embodiment, the therapeutic agent is an activator of at least one TLR. According to another embodiment, the therapeutic agent is an enhancer of at least one TLR. According to another embodiment, the therapeutic agent inhibits at least one TLR. According to another embodiment, the therapeutic agent is an agonist of at least one TLR. According to another embodiment, the therapeutic agent is an antagonist of at least one TLR.

According to one embodiment, a first human gastrointestinal segment is a stomach segment. According to another embodiment, a first human gastrointestinal segment is a jejunum segment. According to another embodiment, a first human gastrointestinal segment is an ileum segment. According to another embodiment, a first human gastrointestinal segment is a duodenum segment. According to another embodiment, a first human gastrointestinal segment is an ascending colon segment. According to another embodiment, a first human gastrointestinal segment is a transverse colon segment. According to another embodiment, a first human gastrointestinal segment is a sigmoid colon segment. According to another embodiment, a first human gastrointestinal segment is a rectum segment.

According to another embodiment, wherein the differentiable gastrointestinal segment-specific human epithelial stem cell-like progenitor cells on the at least one bio-similar matrix environment are used to determine variations in DNA and/or RNA characteristics produced in response to the therapeutic agent.

According to another embodiment, the method further comprises the steps of between step (b) and step (c), serially connecting the bio-similar matrix environment formed from the at least one mucosal tissue derived from the stomach segment to the bio-similar matrix environment formed from the at least one mucosal tissue derived from the jejunum segment to the bio-similar matrix environment formed from the at least one mucosal tissue derived from the ileum segment to the bio-similar matrix environment formed from the at least one mucosal tissue derived from the to the bio-similar matrix environment formed from the at least one mucosal tissue derived from the duodenum segment to the bio-similar matrix environment formed from the at least one mucosal tissue derived from the ascending colon segment to the bio-similar matrix environment formed from the at least one mucosal tissue derived from the transverse colon segment to the bio-similar matrix environment formed from the at least one mucosal tissue derived from the sigmoid colon segment to the bio-similar matrix environment formed from the at least one mucosal tissue derived from the rectum to form an in vitro model of the human gastrointestinal tract; and in step (c) of the method, serially administering the therapeutic agent to the differentiable gastrointestinal segment-specific human stem-cell-like progenitor cells isolated from a human mucosal tissue derived from a human gastrointestinal segment on the serially connected bio-similar matrix environments.

According to another embodiment, the differentiable gastrointestinal segment-specific human epithelial stem cell-like progenitor cell has at least a $\beta$-1-integrin$^{(+)}$cytokeratin$^{(+)}$ phenotype. According to another embodiment, the differentiable gastrointestinal segment-specific human epithelial stem cell-like progenitor cell has a phenotype of cytokeratin(+), $\beta$-1-integrin(+), defensin-5(+), trefoil factor-3(+), mucin-2(+), chomogranin-A(+), intestinal alkaline phosphatase(+), lysozyme(+).

According to another embodiment, the therapeutic target is of a disorder related to altered TLR expression on intestinal epithelial cells and/or mediated signals. These disorders may include, but are not limited to, those of autoimmunity disorders, fungal infections or fungal-associated disorders, such as, but not limited to, aspergillosis, basal cell carcinoma, herpes simplex virus, (HSV-1), encephalitis (HSE), and human primary immunodeficiency.

In one aspect, the described invention provides methods for the isolation of gastrointestinal epithelial stem cell-like progenitor cells located in the gastrointestinal mucosal tissues, growth and differentiation of such cells to specific types of epithelial cell lineages (e.g., columnar epithelium, goblet cell, Paneth cell and/or enteroendocrine chromaffin cells), maintenance of these cells in a non-transformed state, and use of these cells as a model system in drug discovery for TLR related disorders.

Human gastrointestinal epithelial stem-cell-like progenitor cells according to the described invention are derived from mono layers of epithelial cells and can be grown in culture for long periods of time without transformation. Upon establishment of a monolayer, cells are polarized (apical or basolateral) and joined by tight junctions mimicking the actual physiological scenario. The cells can be grown in large quantities and stably stored in liquid nitrogen for extended periods. The gene expression profile of these cells is the same as that observed in the human gastrointestinal epithelium. These cells further may express at least one TLR.

In another aspect, the described invention provides a system to reproducibly characterize the bio availability of a therapeutic agent for a TLR related disorder comprising epithelial monolayers derived from each segment of the gastrointestinal tract, which allows for physiologically relevant regional and/or segmental comparison. It also provides methods for region specific evaluation of absorption and transport of any therapeutic agent. The system provides an accurate representation of the physiological environment of at least one gastrointestinal segment and allows for assessment of specific changes within the gastrointestinal epithelial function early in the drug development timeline. The method comprises several steps.

First, viable human gastrointestinal epithelial stem-cell-like progenitor cells are isolated from at least one segment of the gastrointestinal mucosal tissue of a human subject, wherein the segment of gastrointestinal mucosal tissue comprises a plurality of gastrointestinal mucosal tissue segments. According to one embodiment, gastrointestinal mucosal tissue segments are prepared from the stomach, duodenum, jejunum, ileum, ascending colon, transverse colon, sigmoid, and/or rectum.

Second, a segment-specific bio-similar matrix environment (SS-BSME) is prepared from each segment of the gastrointestinal mucosal tissue. According to one embodiment, an SSBSME prepared from stomach tissue segments is a stomach-specific bio-similar-matrix-environment. According to another embodiment, an SS-BSME prepared from duodenum tissue segments is a duodenum-specific bio-similar-matrix-environment. According to another embodiment, an SS-BSME prepared from jejunum tissue segments is a jejunum-specific bio-similar-matrix-environment. According to another embodiment, an SS-BSME prepared from ileum tissue segments is an ileum-bio-similar-matrix-environment. According to another embodiment, an SS-BSME prepared from colon tissue segments is a colon-specific bio-similar-matrix-environment. According to another embodiment, an SS-BSME prepared from rectum tissue segments is a rectum-specific bio-similar-matrix-environment.

Third, the viable gastrointestinal epithelial stem-cell-like progenitor crypt cells are seeded onto an individual SS-BSME derived from the viable stem-cell-like progenitor crypt cells corresponding to a gastrointestinal mucosal tissue segment.

Fourth, the BSME are incubated to allow for the formation of a monolayer of gastrointestinal epithelial stem-cell-like-progenitor cells.

Fifth, the gastrointestinal epithelial stem-cell-like-progenitor cells of each BSME are treated with a therapeutic agent. The therapeutic agent may be effective for a TLR related disorder.

Sixth, the gastrointestinal epithelial stem-cell-like-progenitor cells of each BSME are analyzed to characterize the bioavailability of the therapeutic agent.

In another aspect, the described invention provides methods to identify therapeutic targets in cells representative of a segment of gastrointestinal mucosa. These cells may express at least one TLR.

According to some embodiments, the individual BSMEs are dispensed into chambers. In some embodiments, the chambers may be culture tubes, Petri dishes, conical tubes, or any type of chamber, container, or vessel that allows propagation and maintenance of cells in vitro. In some embodiments, the chambers may be arranged in any desired order, including, but not limited to, sequentially, randomly, or individually.

According to one embodiment, individual BSMEs are sequentially arranged in the order of a stomach-BSME, a duodenum-BSME, a jejunum-BSME, an ileum-BSME, an ascending colon-BSME, a transverse colon-BSME, a sigmoid-BSME, and a rectum-BSME to mimic the structure of the human gastrointestinal tract. According to other embodiments, the individual BSMEs are formed and utilized separately and/or in discrete subunits where the composition of each subunit is determined by the user.

According to another embodiment, BSMEs are connected to each other via tubes, hoses, valves, check-valves, Y-connectors, connectors or other means suitable for the passage of fluids, vapors, or solids. For example, BSMEs representing each of the segments of the gastrointestinal tract may be connected to each other serially to form an in vitro model of the human gastrointestinal tract. Alternately, selected BSMEs may be connected to each other such that an in vitro model of a portion of the human gastrointestinal tract is formed.

According to another embodiment, each BSME may be polarized, so that it has apical and basolateral surfaces.

According to another embodiment, the electrical resistance of the gastrointestinal epithelial stem-cell-like-progenitor cells is comparable to that of the gastrointestinal epithelial stem-cell-like progenitor crypt cells of the native human gastrointestinal tract. In some such embodiments, TEER values of bio-similar-matrix environments (BSMEs) with gastrointestinal epithelial stem-cell-like progenitor crypt cells is about 25-70 ohm/cm$^2$.

According to another embodiment, the gastrointestinal epithelial stem-cell-like progenitor cells derived from each BSME are genetically modified to a state such that, upon reintroduction into a human patient, the cells are useful for the treatment of gastrointestinal diseases.

According to another embodiment, the cells may express at least one TLR.

In another aspect, the gastrointestinal epithelial stem-cell-like progenitor cells derived from each BSME may be used to assess cellular toxicity of the therapeutic agent effective for treating at least one TLR related disorder. In some embodiments, for example, the gastrointestinal epithelial stem cell-like progenitor cells of the described invention may be used to determine variations in DNA and/or RNA characteristics as related to a response of such cells to a therapeutic agent. As used herein, the term "genomic biomarker" refers to a measurable DNA or RNA characteristic that is an indicator of normal biologic or pathogenic processes or a response to a therapeutic or other interventions. As used herein, the term "pharmacogenomics" refers to the study of variations of DNA and RNA characteristics as related to a drug response, and the term "pharmacogenetics" refers to the study of variations in DNA sequence as related to a drug response. DNA characteristics include, but are not limited to, single nucleotide polymorphisms (SNPs), variability of short sequence repeats, haplotypes, DNA modifications (e.g. methylation), deletions or insertions of (a) single nucleotide(s), copy number variations, and cytogenetic rearrangements (e.g., translocations, duplications, deletions or inversions). RNA characteristics include, but are not limited to, RNA sequences, RNA expression levels, RNA processing (e.g., splicing and editing), and microRNA levels.

In another aspect, the described invention provides a method of making an implantable mucosal scaffold comprising the steps of combining at least two BSMEs such that the stromal tissue underneath is combined with the epithelial mono layers of the gastrointestinal epithelial stem-cell-like progenitor cells derived from each BSME to form a three-dimensional structure of the intestinal mucosa. In one embodiment, the number of different gastrointestinal mucosal tissue segments represented by a corresponding BSME is from about 1 through about 8.

In another aspect, each gastrointestinal epithelial stem-cell-like-progenitor cells-BSME pairing has region specific functional properties. In one embodiment, the gastrointestinal epithelial stem-cell-like-progenitor cells derived from the stomach-BSME have region specific functional properties characteristic of the stomach epithelium. In another embodiment, the gastrointestinal epithelial stem-cell-like-progenitor cells derived from the duodenum-BSME have region specific functional properties characteristic of the duodenum epithelium. In another embodiment, the gastrointestinal epithelial stem-cell-like-progenitor cells derived from the jejunum-BSME have region specific functional properties characteristic of the jejunum epithelium. In another embodiment, the gastrointestinal epithelial stem-cell-like progenitor cells derived from the ileum-BSME have region specific functional properties characteristic of the ileum epithelium. In another embodiment, the gastrointestinal epithelial stem-cell-like-progenitor cells derived from the ascending colon-BSME have region specific functional properties characteristic of the ascending colon epithelium. In another embodiment, the gastrointestinal epithelial stem-cell-like-progenitor cells derived from the transverse colon-BSME have region specific functional properties characteristic of the transverse colon epithelium. In another embodiment, the gastrointestinal epithelial stem-cell-like-progenitor cells derived from the sigmoid-BSME have region specific functional properties characteristic of the sigmoid epithelium. In another embodiment, the gastrointestinal epithelial stem-cell-like-progenitor cells derived from the rectum-BSME have region specific functional properties characteristic of the rectum epithelium. In another embodiment, the gastrointestinal epithelial stem-cell-like-progenitor cells express at least one TLR.

In another embodiment, the permeability of the gastrointestinal epithelial stem-cell-like-progenitor cells-BSME is assayed at about pH 7.4 or with a pH gradient.

In another embodiment, the gastrointestinal epithelial stem-cell-like progenitor cells isolated from gastrointestinal mucosal tissue segments may differentiate into a mature adult cell phenotype. In one such embodiment, the mature cell phenotype is a columnar epithelial cell. In another such embodiment, the mature cell phenotype is a Paneth cell. In another such embodiment, the mature cell phenotype is a goblet cell. In another such embodiment, the mature cell phenotype is an enteroendocrine chromaffin cell. In another such embodiment, the cell is a mesenchymal cell. In another such embodiment, the mature cell phenotype is a neuronal cell type. In one such embodiment, the adult cells express at least one TLR.

In another aspect, the bioavailability of a therapeutic agent is determined by measuring the permeability profile of the gastrointestinal epithelial stem-cell-like-progenitor cells of each BSME. In some such embodiments, the gastrointestinal epithelial stem-cell-like-progenitor cells of each BSME are assayed for permeability of a therapeutic agent of high, medium and/or low solubility. In some such embodiments, the gastrointestinal epithelial stem-cell-like-progenitor cells of each BSME are assayed for permeability of a therapeutic agent in a nonionized and/or ionized form. In some such embodiments, the gastrointestinal epithelial stem-cell-like progenitor cells of each BSME are assayed for permeability of a therapeutic agent in a lipophilic and/or nonlipophilic form. In some such embodiments, the gastrointestinal epithelial stem-cell-like-progenitor cells of each BSME are assayed for permeability of a therapeutic agent resistant and/or non-resistant to gastric juices. In some such embodiments, the gastrointestinal epithelial stem-cell-like-progenitor cells of each BSME are assayed for permeability of a therapeutic agent with and/or without components of protective coatings. In some such embodiments, the gastrointestinal epithelial stem-cell-like-progenitor cells of each BSME are assayed for permeability of a therapeutic agent designed to be controlled-release. In some such embodiments, the gastrointestinal epithelial stem-cell-like-progenitor cells of each BSME are assayed for permeability of a therapeutic agent designed to be extended-release. In some such embodiments, the gastrointestinal epithelial stem-cell-like-progenitor cells of each BSME are assayed for permeability of a therapeutic agent designed to be sustained-release. In some such embodiments, the gastrointestinal epithelial stem-cell-like-progenitor cells of each BSME are assayed for permeability of a therapeutic agent designed to be a prolonged-action pharmaceutical preparation that is designed to produce slow, uniform absorption of the therapeutic agent for 8 hours or longer.

In another aspect of the described invention, a method to identify an effective therapeutic agent to treat a specific disease of the gastrointestinal tract related to a TLR disorder comprises the following steps. First, viable gastrointestinal epithelial stem-cell-like progenitor cells are isolated from the gastrointestinal mucosal tissues of a human subject, wherein the gastrointestinal mucosal tissue is comprised of gastrointestinal mucosal tissue segments, wherein at least one of the gastrointestinal mucosal tissue segments is in a diseased state. Second, SS-BSMEs are prepared from each gastrointestinal mucosal tissue segment. Third, the viable gastrointestinal epithelial stem-cell-like-progenitor cells are seeded onto the SS-BSME derived from the gastrointestinal epithelial stem-cell-like-progenitor cells. Fourth, the BSMEs are incubated to allow for the formation of a monolayer of gastrointestinal epithelial stem-cell-like-progenitor cells. Fifth, the gastrointestinal epithelial stem-cell-like-progenitor cells of each BSME are exposed to a candidate therapeutic agent. Sixth, the gastrointestinal epithelial stem-cell-like-progenitor cells of each BSME are analyzed to identify a desired therapeutic effect.

In another aspect, the described invention provides a method to ascertain regional specificity of a therapeutic agent useful in treating disorders of the gastrointestinal tract related to a TLR disorder. The method comprises several steps. First, viable gastrointestinal epithelial stem-cell-like-progenitor cells are isolated from the gastrointestinal mucosal tissues of a human, wherein the gastrointestinal mucosal tissue is comprised of gastrointestinal mucosal tissue segments. Second, an individual BSME is formed from each gastrointestinal mucosal tissue segment. Third, the viable gastrointestinal epithelial stem-cell-like-progenitor cells are seeded onto an individual BSME derived from the viable gastrointestinal epithelial stem-cell-like-progenitor cells. Fourth, the BSMEs are incubated to allow formation of a monolayer of the gastrointestinal epithelial stem-cell-like-progenitor cells. Fifth, each BSME is treated with a therapeutic agent. Sixth, the gastrointestinal epithelial stem-cell-like-progenitor cells of each BSME are analyzed to determine regional specificity of the therapeutic agent.

In some embodiments, the gastrointestinal epithelial stem-cell-like-progenitor cells demonstrate regional specificity characteristic of areas of the small intestine. In some embodiments, the gastrointestinal epithelial stem-cell-like-progenitor cells demonstrate regional specificity characteristic of at least areas of the large intestine. In some embodiments, the gastrointestinal epithelial stem-cell-like-progenitor cells demonstrate regional specificity characteristic of at least areas of the stomach. In some embodiments, the gastrointestinal epithelial stem-cell-like-progenitor cells demonstrate regional specificity characteristic at least of areas of the duodenum. In some embodiments, the gastrointestinal epithelial stem-cell-like-progenitor cells demonstrate regional specificity characteristic at least of areas of the jejunum. In some embodiments, the gastrointestinal epithelial stem-cell-like-progenitor cells demonstrate regional specificity characteristic at least of areas of the ileum. In some embodiments, the gastrointestinal epithelial stem-cell-like-progenitor cells demonstrate regional specificity characteristic at least of areas of the ascending colon. In some embodiments, the gastrointestinal epithelial stem-cell-like-progenitor cells demonstrate regional specificity characteristic at least of areas of the transverse colon. In some embodiments, the gastrointestinal epithelial stem-cell-like-progenitor cells demonstrate regional specificity characteristic at least of areas of the sigmoid colon. In some embodiments, the gastrointestinal epithelial stem-cell-like-progenitor cells demonstrate regional specificity characteristic at least of areas of the rectum. In some embodiments, the cells express at least one TLR.

Gastrointestinal epithelial stem-cell-like progenitor cells may be propagated in vitro by providing a suitable surface and a suitable mixture of soluble factors. An autologous composition of growth factors derived from corresponding mucosal tissue, along with mucosal tissue obtained gastrointestinal epithelial stem-cell-like progenitor cells, are required for viable growth and differentiation of the stem-cell-like progenitor crypt cells.

It has been found that gastrointestinal epithelial stem-cell-like progenitor cells grown in bio-similar-matrix-environments grow to form viable mono layers while retaining normal cellular characteristics. The cells may express at least one TLR.

General methods in molecular genetics and genetic engineering useful in the described invention are described in the current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found in Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al. eds., Wiley & Sons.). Reagents, cloning vectors, and kits for genetic manipulation are available from commercial vendors, such as BioRad, Stratagene, Invitrogen, ClonTech, and Sigma-Aldrich Co.

Cell culture methods useful in the described invention are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other relevant texts are Creating a High Performance Culture (Aroselli, Hu. Res. Dev. Pr. 1996) and Limits to Growth (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a," "and," and "the" include plural references unless the context clearly dictates otherwise. All technical and scientific terms used herein have the same meaning.

Publications discussed herein are provided solely for their disclosure prior to the filing date of the described application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Aspects of the present invention are improvements over the disclosures made by applicant in U.S. patent application Ser. No. 12/428,866, filed Apr. 23, 2009, published as US-2009/0269769 on Oct. 29, 2009, which corresponds to International Application No. PCT/US2009/041549, filed Apr. 23, 2009, published as WO-2009/132196 on Oct. 29, 2009, the entire disclosures of which are hereby incorporated by reference herein.

Aspects of the present invention are also improvements over the disclosures made by applicant in U.S. patent application Ser. No. 12/577,141, filed Oct. 9, 2009, published as US-2010/0093552 on Apr. 15, 2010, which corresponds to International Application No. PCT/US2009/060285, filed Oct. 9, 2009, published as WO-2010/042903 on Apr. 15, 2010, the entire disclosures of which are hereby incorporated by reference herein.

Example 1

Figure 9:
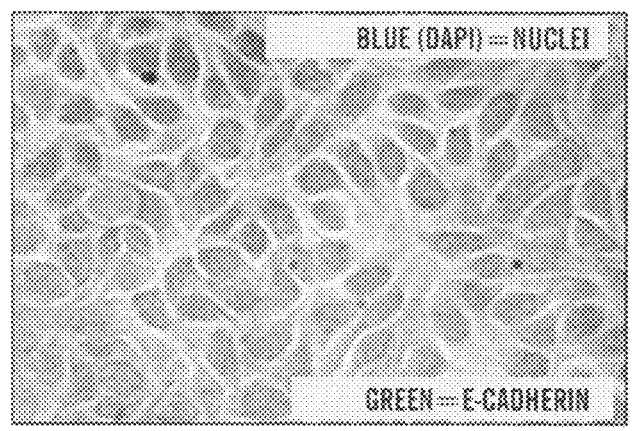
FIG. 9 shows a micrograph of a monolayer formed by isolated human gastrointestinal epithelial stem cell derived progenitor cells on a biosimilar matrix. Immunofluorescence staining (green) of cell:cell junction forming protein E-cadherin and DAPI staining (blue) of the nucleus of the cells in the monolayer.
Figure 10A:
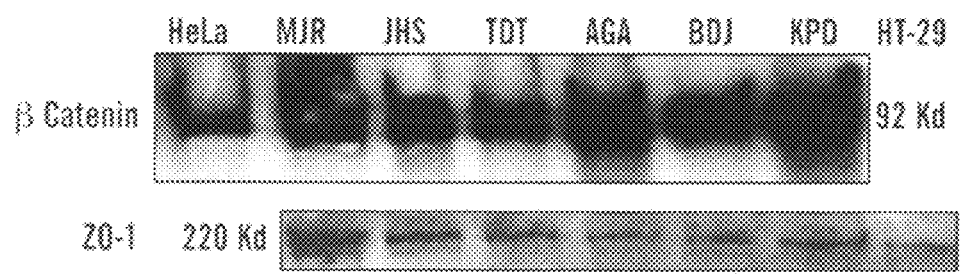
FIGS. 10A and 10B show junction protein expression in HIPEC monolayers.
Figure 10B:
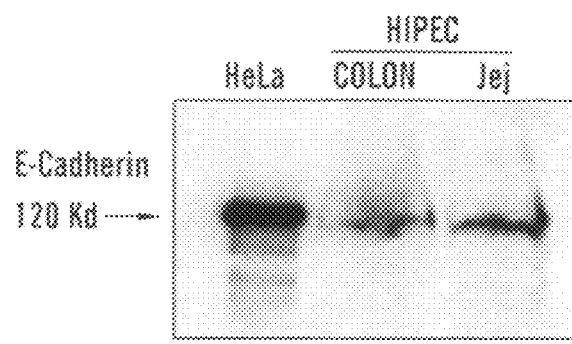

Isolation, Culturing, and Demonstration of Stem Cell Characteristics of Cells Isolated from Adult Human Gastrointestinal Tissues Applicant isolated stem cells from adult GI tissues and derived differentiated epithelial cells from them. Stem cells from the esophagus, stomach, duodenum, jejunum, ileum, cecum, ascending colon, transverse colon, sigmoid, and rectum of an adult human were isolated and cultured. The identification of these cells as stem cells was verified via demonstration of three aspects of their nature. In particular, these cells were analyzed for their (i) expression of known stem cell markers (see FIG. 1); (ii) self-renewal (see FIG. 3); and (iii) pluripotency (see FIG. 2, FIG. 5, FIG. 6, FIG. 8A, FIG. 8B, FIG. 11, and FIG. 12). Also see FIG. 9 and FIG. 10.

Suitable materials and methods relating to aspects of producing the ahGISC lines and HIPEC lines of the present invention are described by applicant in its disclosures set forth in US-2009/0269769 and/or US-2010/0093552, the entire disclosures of which are hereby incorporated by reference herein.

Expression of appropriate stem cell markers by GI stem cell lines: In one experiment, RT-PCR of total RNA prepared from stem cell lines cultured from 10 regions/tissues of the GI tract (see FIG. 1). All lines were positive for stem cell markers Nanog, LIN28, Oct4 (4th panel down—represents both variant-1 and -2, 5th panel down-variant-2, and 6th panel down-variant-1), and SOX2, though esophagus SOX2 expression was very low (FIG. 1). While stem cell lines derived from all tissues demonstrated expression of Bmi1, the duodenum, jejunum, and transverse colon were negative for putative intestinal stem cell marker Lgr5. This may indicate the regional specificity of stem cell marker expression profiles of various segments of the GI tract. Total RNA obtained directly from the same jejunum tissue from which the jejunum stem cell line was derived was also negative for Lgr5.

As indicated above, results are shown in FIG. 1. All lines demonstrated some variable level expression of TLR1, TLR2, TLR4, TLR5, TLR6, TLR10, and myD88. Rectal derived stem cells showed very low levels of TLR4 and myD88.

Demonstration of stem cell lines' "self-renewal": In one experiment, RT-PCR of total RNA prepared from stem cell line developed by applicant from a section of jejunum and cultured for 20 passages (10 shown) (see FIG. 3). The jejunum stem cell line continued to replicate and express the stem cell markers Oct4 and Nanog: demonstrating not only stability in culture, but also the ability to maintain its "self-renewal" characteristic during repeated cell divisions in culture. RT-PCR reactions were performed with equal amounts of total RNA and samples were further equilibrated based upon their b-tubulin amplification results.

Demonstration of cultured stem cell's pluripotency: The cultured ahGISC lines were determined to have pluripotency (see FIG. 2, FIG. 5, FIG. 6, FIG. 8A, FIG. 8B, FIG. 11, and FIG. 12). Phase images of representative HIPEC lines derived from various segments of the intestine: (A) duodenum, (B) jejunum, (C) ascending colon, (D) transverse colon, (E) sigmoid, and (F) rectum (FIG. 5). All human intestinal primary epithelial cell (HIPEC) lines were derived from stem cell lines established from resected specimens obtained from the normal portions of GI tissue from various patients.

Figure 8B:
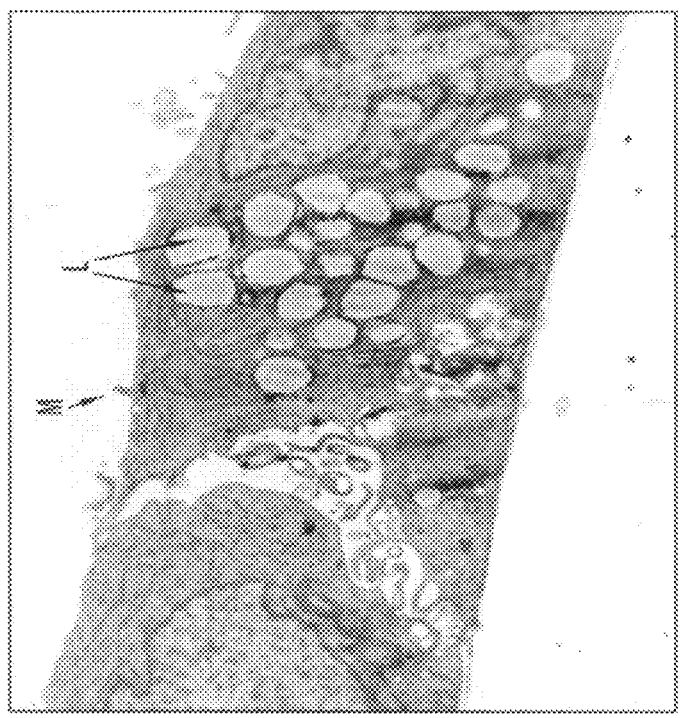
FIGS. 8A and 8B show electron micrographs of one representative adult human oral mucosal stem cell derived non-transformed primary epithelial cell line grown on transwell membrane (Costar).
Figure 8A:
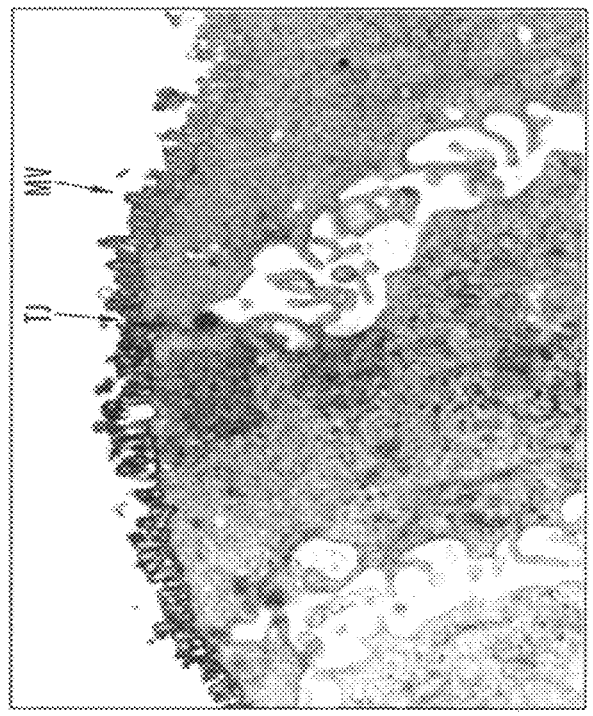

Electron microscopy of a representative HIPEC line at passage 4. At passage 4, electron microscopy was conducted with respect to a representative HIPEC line of the present invention. As shown in FIG. 8A, microvilli (MV) are present on the apical surface of cells which contain large nuclei, bundles of microfilaments, and intercellular tight junction (TJ). As shown in FIG. 8B, Goblet cells are also present and are readily identified by their scant microvilli (M) and numerous mucin containing vesicles (L).

Figure 2:
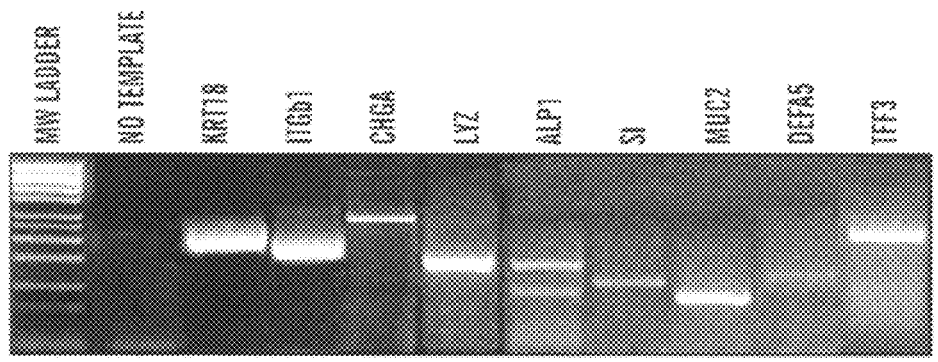
FIG. 2 shows an agarose gel of the RT-PCR products of a total RNA preparation from small intestine derived HIPEC cell line A2J1. Lane: (1) molecular weight markers; (2) no template control; (3) KRT18; (4) ITGb1; (5) CHGA; (6) LYZ; (7) ALP1; (8) SI; (9) MUC2; (10) DEFA5; and (11) TFF3.
Figure 3:
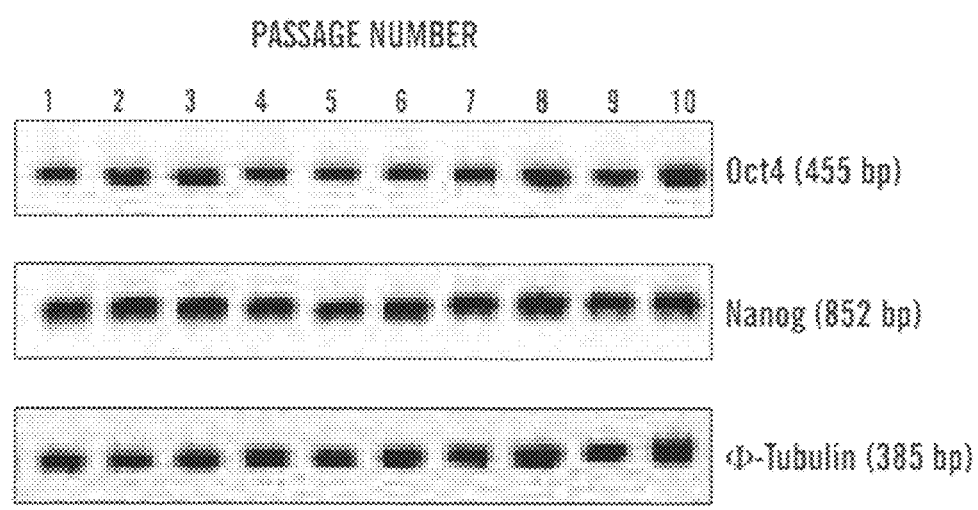
FIG. 3 shows agarose gels for the biomarker Oct4, Nanog, and β-tubulin RT-PCR amplification products acquired during each serial passage of the A2J1 stem cell line. Ten of the twenty passages are shown.
Figure 4:
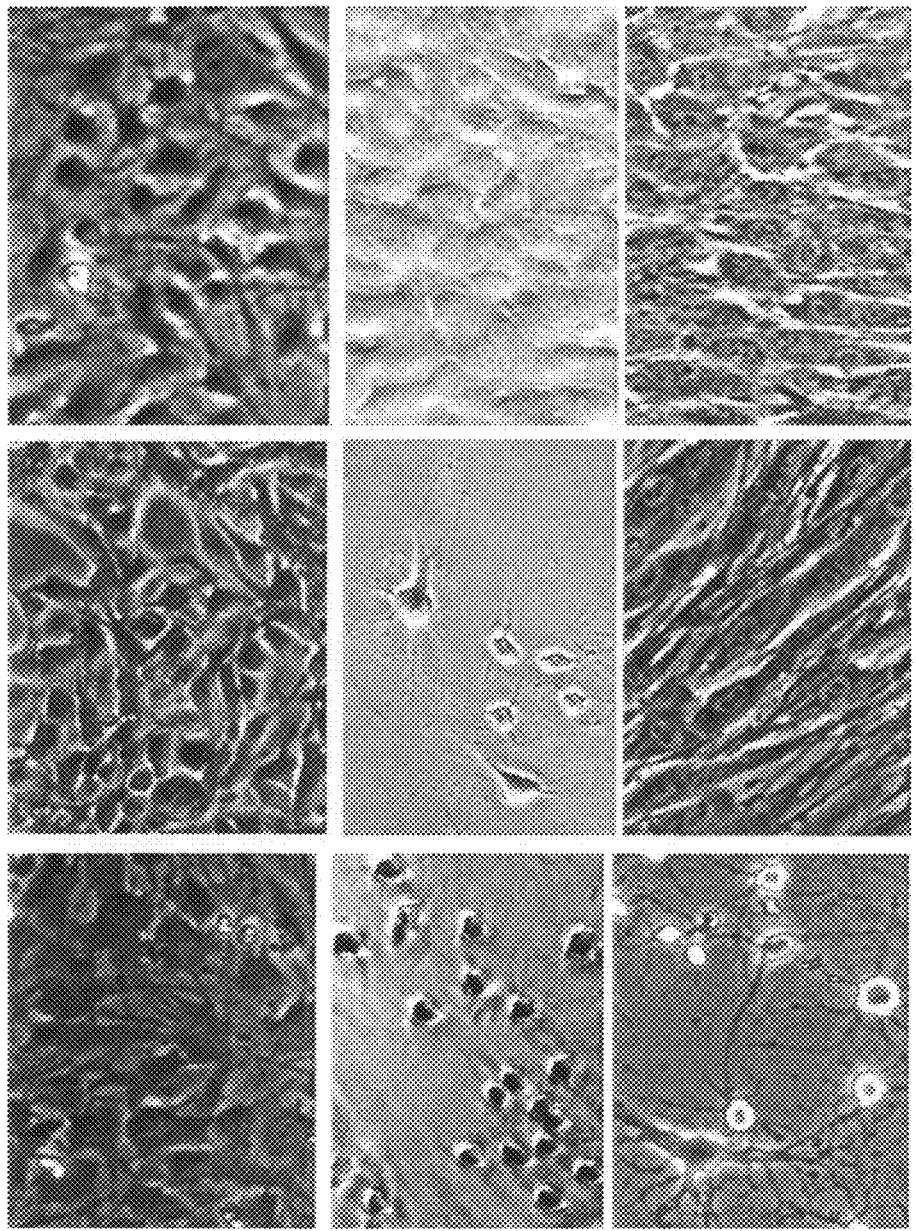
FIG. 4 shows light microscope phase contrast images of representative HIPEC cell lines derived from hGISC lines.
Figure 5A:
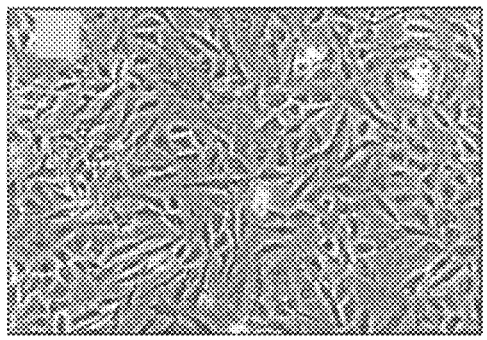
FIG. 5 shows light photomicrographs of one embodiment of primary epithelial monolayers derived from human gastrointestinal stem-cell-like progenitor cells isolated from various segments of the human gastrointestinal tract. (A) duodenum; (B) jejunum; (C) ascending colon; (D) transverse colon; (E) sigmoid; and (F) rectum. All colonic HIPEC lines were derived from the normal portion of a resected specimen from patients suffering different disorders.
Figure 5D:
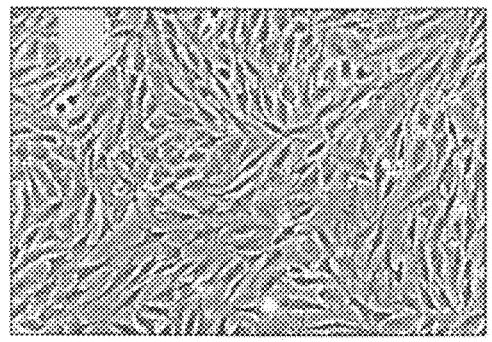
Figure 5B:
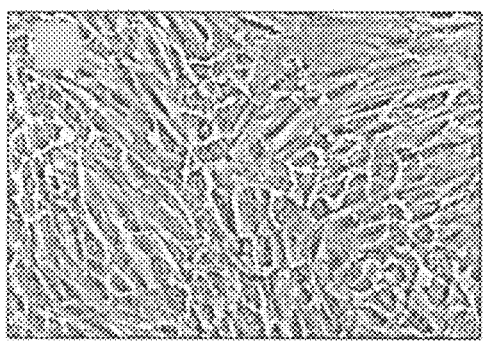
Figure 5E:
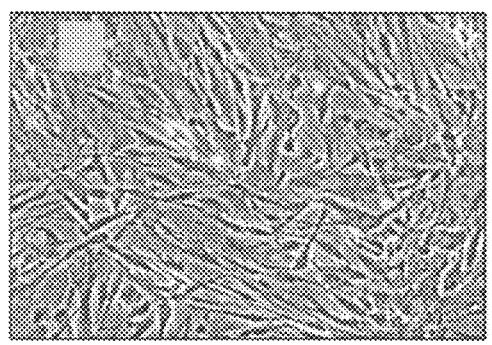
Figure 5C:
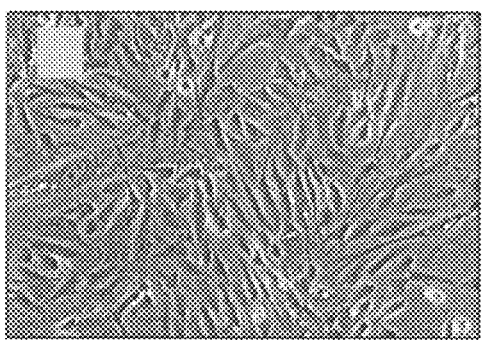
Figure 5F:
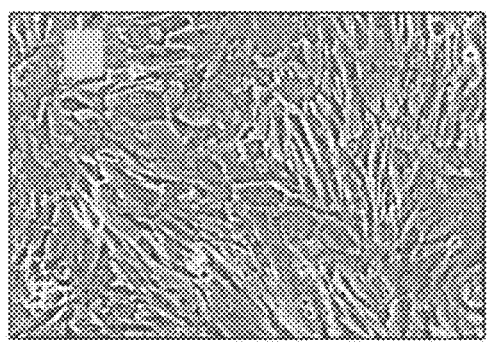

Expression of epithelial markers. As shown in FIG. 2, RT-PCR products of a total RNA prep from a small intestine derived HIPEC cell line A2J1 was conducted. The cell line demonstrated expression of epithelial markers cytokeratin-18 (KRT18) and β1 integrin (ITGb1), enteroendocrine marker chromogranin A(CHGA), both Paneth markers lysozyme (LYZ) and defensin-5 (DEFA5), both enterocyte markers intestinal alkaline phosphatase (ALP1) and sucrase isomaltase (SI), and both Goblet markers mucin-2 (MUC2) and trefoil factor 3 (TFF3).

Figure 6A:
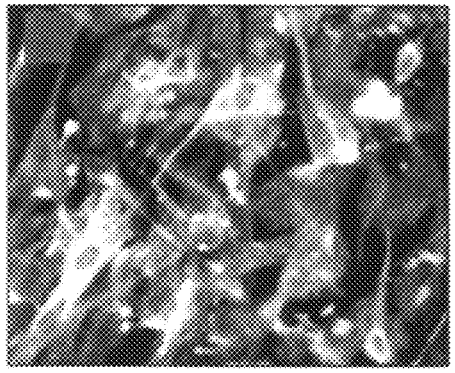
FIG. 6 shows immunohistochemical staining of HIPEC lines using antibodies against cytokeratin-18. (A) duodenum; (B) jejunum; (C) ascending colon; (D) transverse colon; (E) sigmoid; and (F) rectum.
Figure 6D:
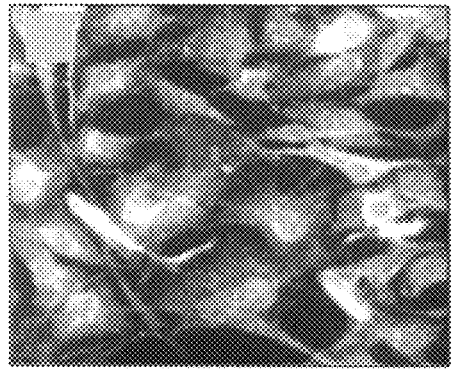
Figure 6B:
Figure 6E:
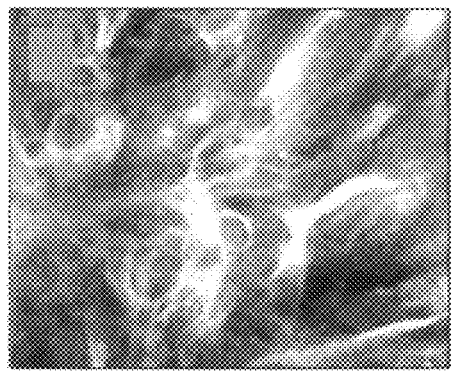
Figure 6C:
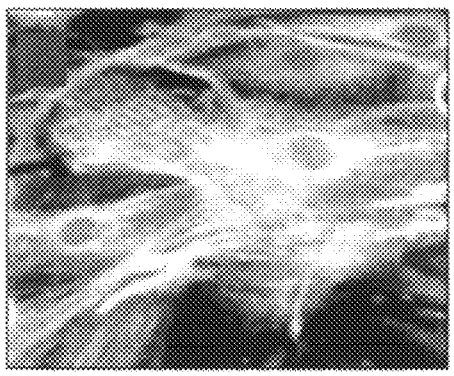
Figure 6F:
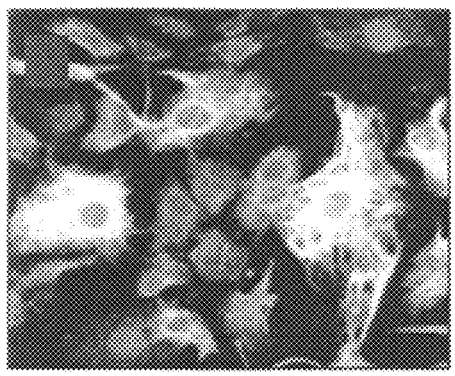

Analysis of cytokeratin (CK) in HIPEC lines derived from various GI tissues: As shown in FIG. 6, the HIPEC lines derived from the following tissues were analyzed for cytokeratin (CK): duodenum (FIG. 6A); jejunum (FIG. 6B); ascending colon (FIG. 6C); transverse colon (FIG. 6D); sigmoid (FIG. 6E); and rectum (FIG. 6F). Dissociated cells from HIPEC mono layers were stained with anti-cytokeratin-18. All cells were positive for cytokeratin.

Figure 11A:
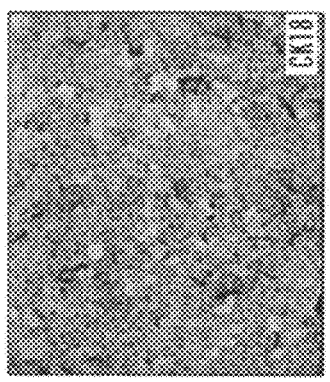
FIGS. 11A-11G show micrographs of mixed HIPEC cell lines showing cells immunohistochemically stained with antibody for CK18 (FIG. 11A), EP4 (FIG. 11B), SC (FIG. 11C), MUC2 (FIG. 11D), MUC2/phase (FIG. 11E), lysozyme/DAPI (FIG. 11F), and SSTR5/DAPI (FIG. 11G).
Figure 11B:
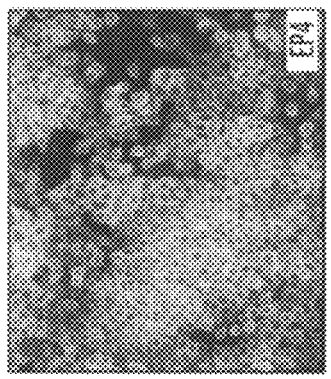
Figure 11C:
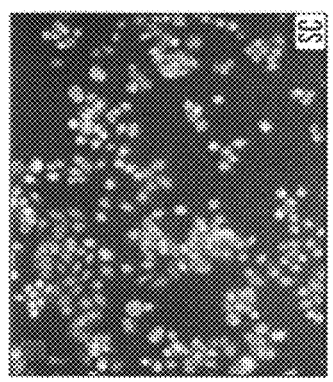
Figure 11D:
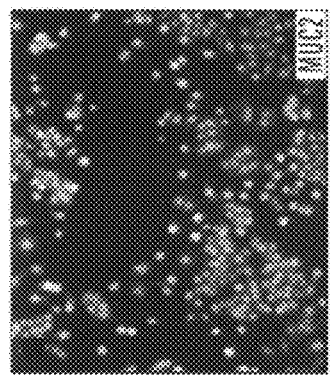
Figure 11E:
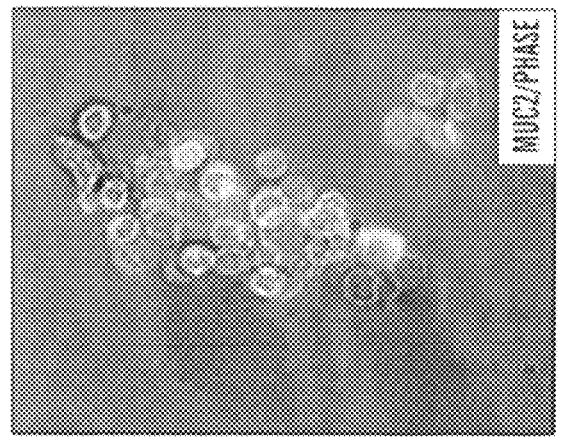
Figure 11F:
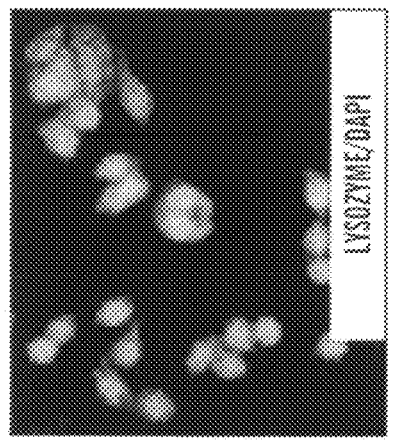
Figure 11G:
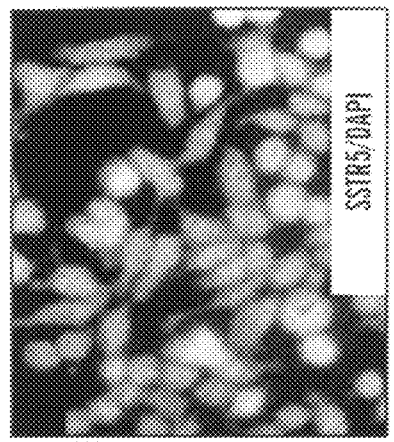

IC staining of HIPEC lines for epithelial lineage specific protein expression. As shown in FIG. 11A and FIG. 11B, the vast majority of cells were shown to be positive to varying degrees for epithelial markers cytokeratin-18 (CK18) and epithelial protein 4 (EP4). As shown in FIG. 11C, FIG. 11D, and FIG. 11E, a smaller subset of cells were positive for Goblet cell specific secretory component (SC) and mucin-2 (MUC2).

Figure 7:
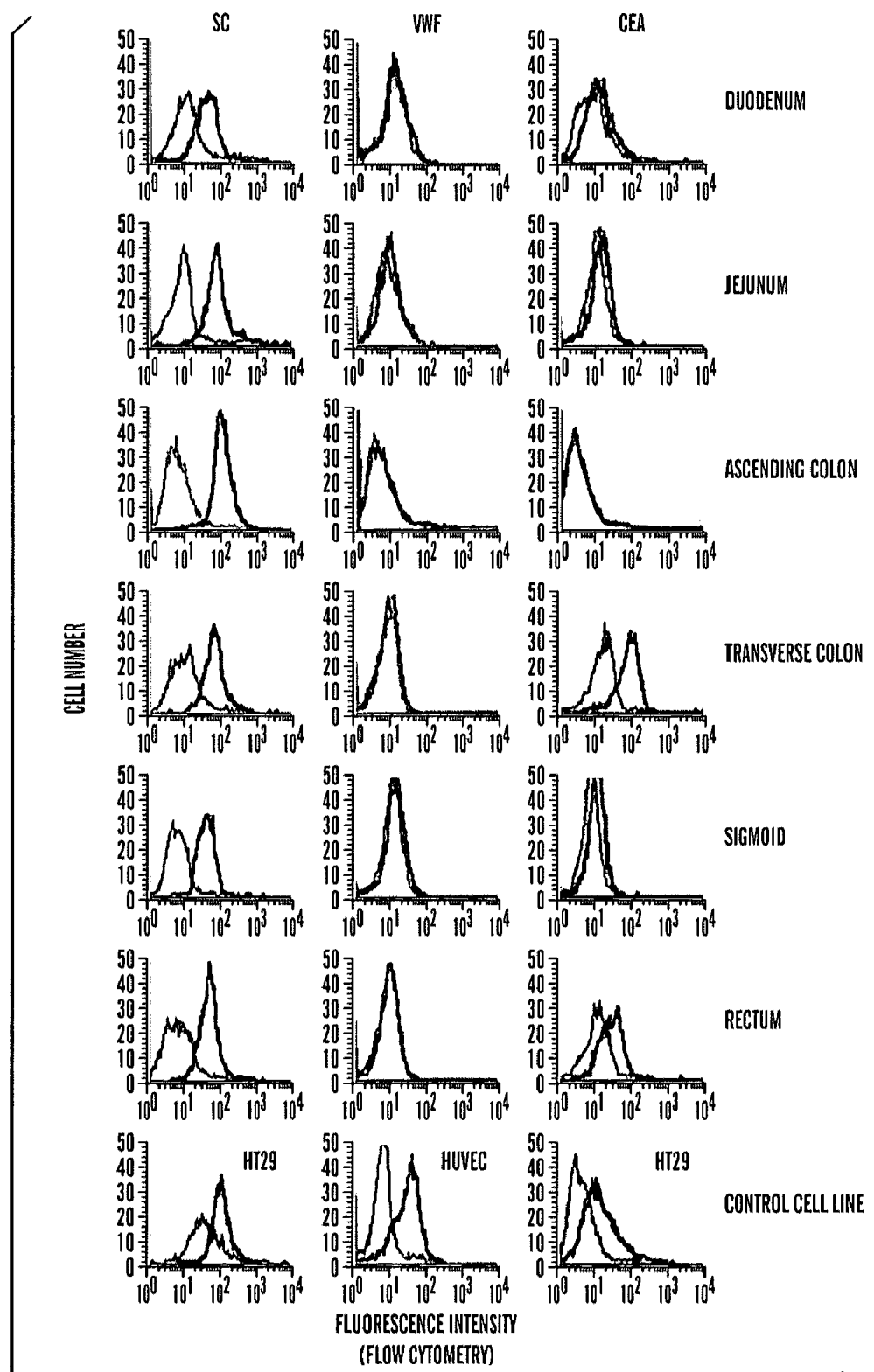
FIG. 7 shows plots of the flow cytometric analysis of the cells stained with an anti-CEA (right panel—red lines), anti-VWF (middle panel—green lines), anti-SC (left panel—blue lines), or control antibody (black lines). For the detection of SC, staining was performed on unpermeabilized cells. All HIPEC lines were positive for secretory component (left panel) and negative for VWF (middle panel) and SMC (data not shown). Variable level of CEA expression (right panel) was observed. The bottom panel row are control cell lines: the colonic adenocarcinoma cell line HT29 used to demonstrate both SC (left panel) and CEA (right panel) expression and a endothelial cell line, HUVEC (center panel) used to demonstrate VWF expression.
Figure 12:
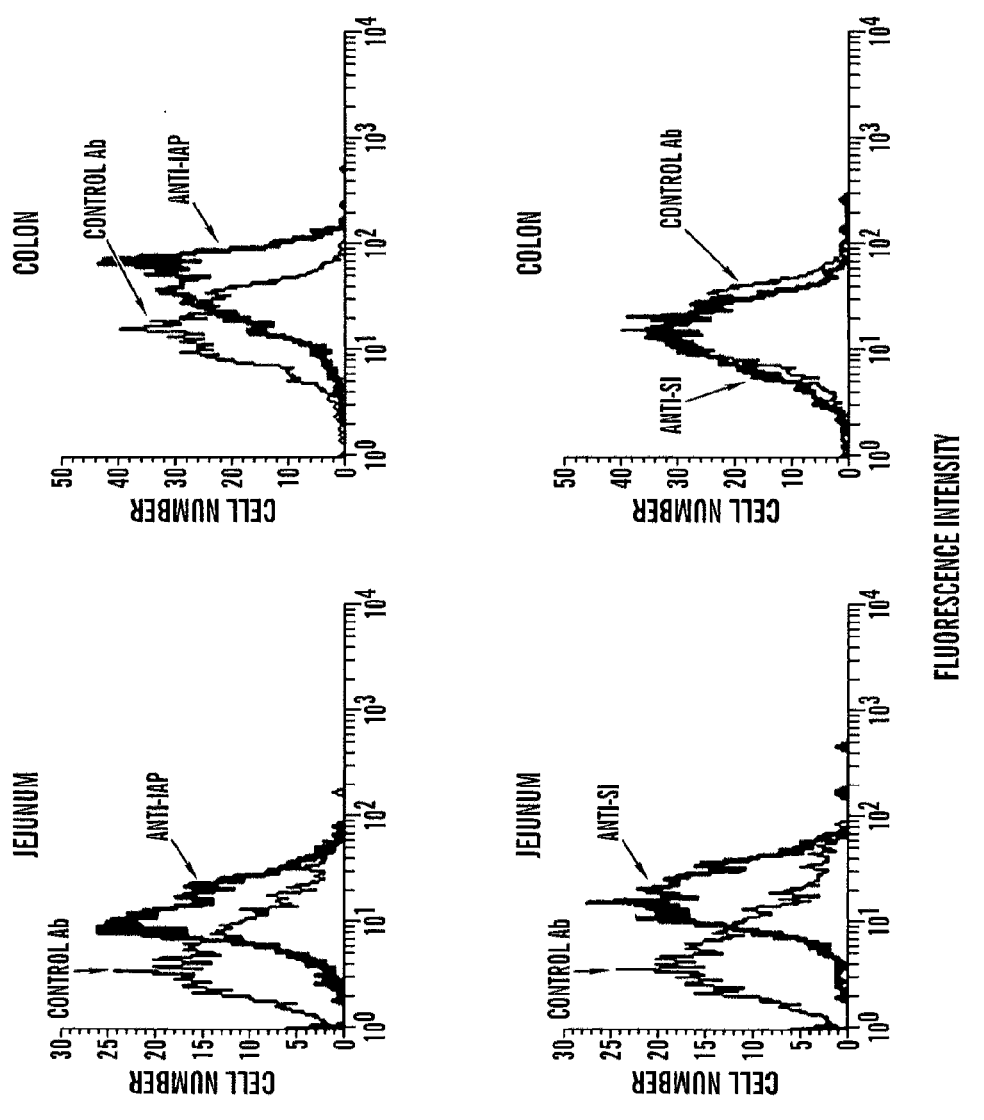
FIG. 12 shows a plot of fluorescence intensity versus cell number of HIPEC lines expressing intestine specific enzyme markers intestinal alkaline phosphatase (IAP) and sucrase isomaltase (SI). Immunofluorescence staining of representative HIPEC lines from small (jejunum (left panel)) and large (colon (right panel)) intestine with anti-human intestinal alkaline phosphatase (upper panel) and sucrase isomaltase (lower panel).
Figure 13:
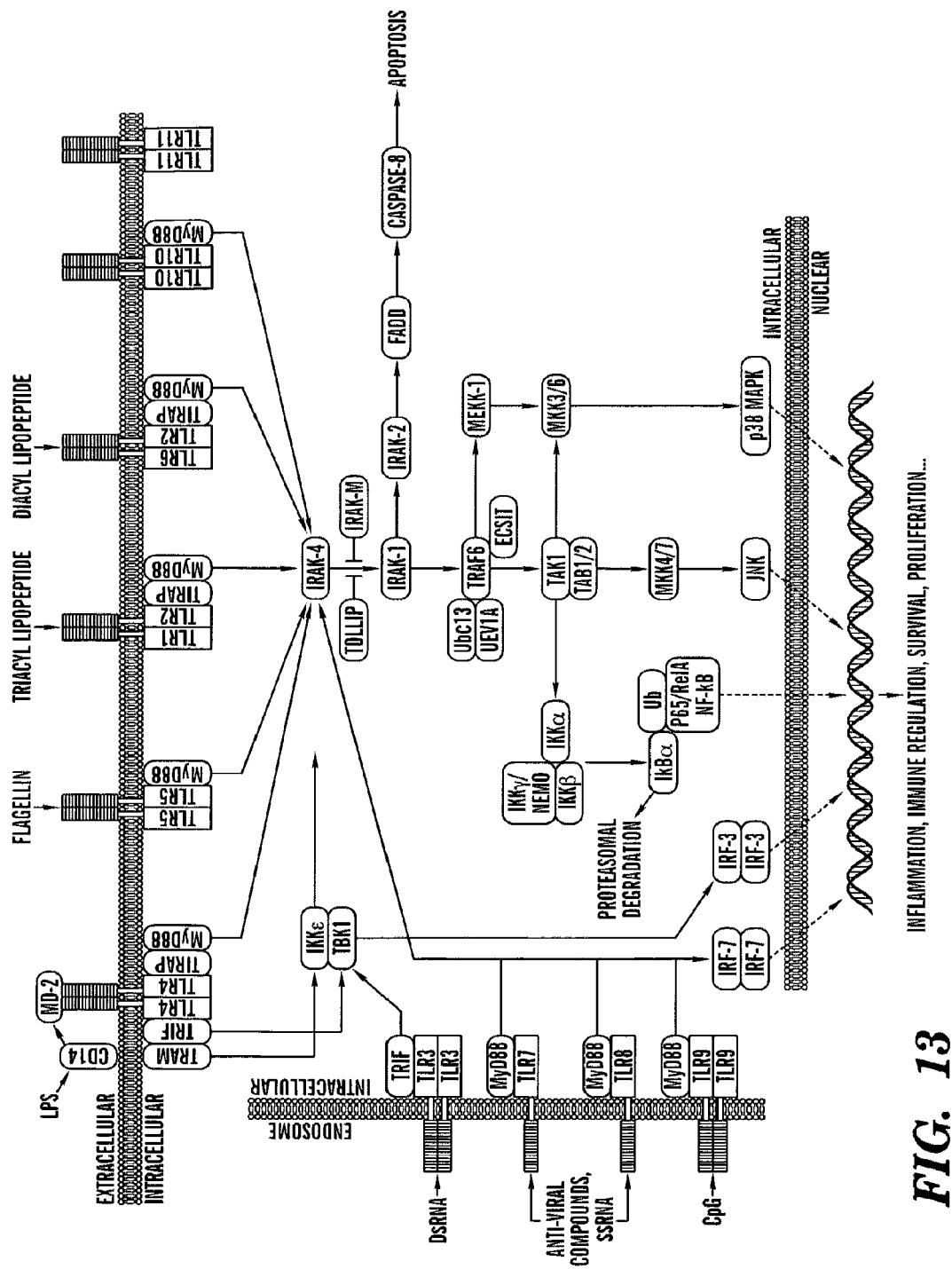
FIG. 13 shows a schematic drawing of signaling pathways of Toll-like receptors (TLRs).

Flow cytometric analysis of epithelia marker expression of HIPEC lines derived from jejunum (A2J1 cell line) and colon (5A cell line) tissue sources. GI segment specific expression of epithelial markers by derived HIPEC lines mimicking their in vivo expression patterns was observed. FIG. 12 shows that jejunum and colon derived HIPECs, derived by applicant according to the present invention, both expressed intestinal alkaline phosphatase (IAP), but only the jejunum derived line expresses sucrase isomaltase (SI), similar to the in vivo state. Similar results were observed by other independent studies evaluating the same cell lines, for carbonic anhydrase (CA) expression. The observed CA expression in the jejunum cell line and lack thereof in the colon derived stem cell line is indicative of the native in vivo state, whereas, both the transformed colon derived cell lines, HT-29 and Caco-2, clearly demonstrated inappropriate expression of CA. Most GI diseases and many non-GI diseases are the result of a dysfunctional epithelium. Based on these findings, the intestinal primary epithelial cell system of the present invention is a cellular platform that provides close resemblance to the in vivo state, thereby providing superior results over exiting systems. Also see FIG. 7 for additional flow cytometry data.

Example 2

Toll-Like Receptor Expression Analysis

In various experiments, in order to study TLR expression in the ahGISC and HIPEC lines as well as to develop TLR expression profiles therein, standard expression techniques known in the art were conducted.

For various TLR immunohistochemical staining analyses of the ahGISC and HIPEC lines of the present invention, the following antibodies were used: anti-TLR2 mouse monoclonal (Abcam Cat. #ab9100) (Abcam Inc., Cambridge, Mass.); anti-TLR4 (Abcam Cat. #ab30667) (Abcam Inc., Cambridge, Mass.); and anti-TLR6 (Abcam Cat. #ab72361) (Abcam Inc., Cambridge, Mass.). Other antibodies directed to the various other TLRs disclosed herein may also be used for TLR immunohistochemical staining analyses of the ahGISC and HIPEC lines of the present invention.

In studying TLR expression of the ahGISC and HIPEC lines that express TLR, and in determining the TLR expression profile of the cell lines, RT-PCR reactions and incubations were performed in a thermocycler. The primers and thermocycler protocols utilized are shown in Table 2 (upstream/sense primers); Table 3 (downstream/antisense primers; and Table 4 (thermocycler PCR parameters), as shown below.

TABLE 2

PCR Primers for TLR Expression Analyses: Upstream/Sense Primers

| Gene Target | Designation | Primer Sequence (5'→3') | SEQ ID NO |
|---|---|---|---|
| Nanog | hNanog-2f | ATGCCTGTGATTTGTGGGCC | 1 |
| L1N28 | hLIN28-1f | CAACCAGCAGTTTGCAGGTGGCTG | 2 |
| Oct4 (variant 1 and 2) | hOct4f-2 | CATCAAAGCTCTGCAGAAAGAACTC | 3 |
| Oct4 (variant 1) | hOct4f-4 | CGGGACACCTGGCTTCGGATTTCG | 4 |
| Oct4 (variant 2) | hOct4f-5 | CATGAGTCAGTGAACAGGGAATG | 5 |
| SOX2 | hSOX2-6f | CAAAAGTCTTTACCAATAATATTTAGAG | 6 |
| SOX2 | hSOX2-5f | TAAAAGTTCTAGTGGTACGGTAGGAG | 7 |
| Bmi1 | bmi-f1 | CATAATAGAATGTCTACATTCCTTCTG | 8 |
| LGR5 | hLGR5-8f | GATCTGTCTTACAACCTATTAGAAG | 9 |
| β-tubulin | BT8 | CTGAAAACACATGTAGATAATGGC | 10 |
| TLR1 | hTLR1f-4 | GTTCTTGGACTAAAAGTTTATTAAG | 11 |
| TLR2 | hTLR2f-2 | CTTATCCAGCACACGAATACACAG | 12 |
| TLR4 | hTLR4f | TGGATACGTTTCCTTATAAG | 13 |
| TLR6 | hTLR6f | TTGGACTCATATCAAGATGCTCTG | 14 |
| TLR10 | hTLR10f | ATGCTTTTCCCGAATTATCCTACG | 15 |
| myD88 | myD88f-2 | CTCCAGGACCGCCCGCCATGGCTA | 16 |
| IL8 | IL8-1 | CTGTGTGTAAACATGACTTCCAAG | 17 |

TABLE 3

PCR Primers for TLR Expression Analyses: Downstream/Anti-sense Primers

| Gene Target | Designation | Primer Sequence (5'→3') | SEQ ID NO |
|---|---|---|---|
| Nanog | hNanog-6r | CTCATCTTCACACGTCTTCAGGTTG | 18 |
| LIN28 | hLIN28-5r | GAACCCTCACTTGCATTTGGACAGAG | 19 |
| Oct4 (variant 1 and 2) | hOct4r-3 | CTGCTTGATCGCTTGCCCTTCTGGC | 20 |
| Oct4 (variant 1) | hOct4r-5 | CTTGTAAGAACATAAACACACCAG | 21 |
| Oct4 (variant 2) | hOct4r-z | GGTTTCTGCTTTGCATATCTCCTG | 22 |
| SOX2 | hSOX2-7r | GCCGAATCTTTTAAAATACAACTACG | 23 |
| SOX2 | hSOX2-7r | Same as above | Same |
| Bmi1 | bmi-r4 | GGAAGTGGACCATTCCTTCTCCAG | 24 |
| LGR5 | hLGR5-3r | CTTCAAGGTCACGTTCATCTTGAGC | 25 |
| β-tubulin | BT8R | CTGGAGGCTTAGGGACCAAGGCTG | 26 |
| TLR1 | hTLR1r-3 | GTGATAACTGCTAGGAATGGAGTAC | 27 |
| TLR2 | hTLR2r | TTGAAGTTCTCCAGCTCCTG | 28 |
| TLR4 | hTLR4r | GAAATGGAGGCACCCCTTC | 29 |
| TLR6 | hTLR6r | TCAGAATTTGTAGACTTTCTGTCTC | 30 |
| TLR10 | hTLR10r | CAACCATCATGACCTCTGAATATG | 31 |
| myD88 | myD88r-3 | GTTCCAGTTGCCGGATCATCTCCTG | 32 |

TABLE 3-continued

PCR Primers for TLR Expression Analyses: Downstream/Anti-sense Primers

| Gene Target | Designation | Primer Sequence (5'→3') | SEQ ID NO |
|---|---|---|---|
| IL8 | IL8-6 | GAATTTTTTATGAATTCTCAGC-CCTC | 33 |
| Oligo dT (20 mer) | (dT)20 | TTTTTTTTTTTTTTTTTTTT | 34 |

TABLE 4

PCR Thermocycler Protocols for TLR Expression Analyses

| | | PCR Parameters | | | | | | |
|---|---|---|---|---|---|---|---|---|
| | PCR | Denaturation Step | | Annealing Step | | Extension Step | | # |
| Gene Target | Product Size (bp) | Temp (° C.) | Duration (min:sec) | Temp (° C.) | Duration (min:sec) | Temp (° C.) | Duration (min:sec) | of Cycles |
| Nanog | 852 | 94.0 | :40 | 56.0 | :30 | 73.0 | 1:00 | 35 |
| LIN28 | 828 | 94.0 | :40 | 56.0 | :30 | 73.0 | 1:00 | 35 |
| Oct4 (variant 1 and 2) | 455 | 94.0 | :40 | 56.0 | :30 | 73.0 | :45 | 30 |
| Oct4 (variant 1) | 828 | 94.0 | :40 | 56.0 | :30 | 73.0 | 1:00 | 35 |
| Oct4 (variant 2) | 471 | 94.0 | :40 | 56.0 | :30 | 73.0 | :45 | 40 |
| SOX2 | 581 | 94.0 | :40 | 56.0 | :30 | 73.0 | :45 | 35 |
| SOX2 | 621 | 94.0 | :40 | 56.0 | :30 | 73.0 | :45 | 35 |
| Bmi1 | 576 | 94.0 | :40 | 56.0 | :30 | 73.0 | :45 | 40 |
| LGR5 | 498 | 94.0 | :40 | 56.0 | :30 | 73.0 | :45 | 40 |
| β-tubulin | 385 | 94.0 | :40 | 56.0 | :30 | 73.0 | :45 | 30 |
| TLR1 | 976 | 94.0 | :40 | 56.0 | :30 | 73.0 | 1:00 | 30 |
| TLR2 | 676 | 94.0 | :40 | 56.0 | :30 | 73.0 | 1:00 | 30 |
| TLR4 | 514 | 94.0 | :40 | 56.0 | :30 | 73.0 | 1:00 | 30 |
| TLR6 | 643 | 94.0 | :40 | 56.0 | :30 | 73.0 | 1:00 | 30 |
| TLR10 | 615 | 94.0 | :40 | 56.0 | :30 | 73.0 | 1:00 | 30 |
| myD88 | 566 | 94.0 | :40 | 56.0 | :30 | 73.0 | 1:00 | 30 |
| IL8 | 319 | 94.0 | :40 | 56.0 | :30 | 73.0 | :30 | 30 |

Example 3

Differential TLR Expression Profile in Both Epithelial Stem Cells (Epi-SC) Isolated from Each Segment of The Human Intestinal Tract and Primary NonTransformed Epithelial Cell Lineages Derived from the Cultured Epi-SCs In various experiments, studies were conducted to develop a differential TLR expression profile in both epithelial stem cells (Epi-SC) isolated from each segment of the human intestinal tract and primary non-transformed epithelial cell lineages derived from the cultured Epi-SCs.

As discussed herein, Toll-like Receptors (TLRs) are transmembrane proteins that recognize pathogen associated molecular patterns (PAMPs) and activate the innate immune system against invading microbes. The luminal surface of the gastrointestinal epithelium is the largest area in the body exposed to a myriad of microbial species on a constant basis. While site preference (e.g., small vs. large intestine) for many infectious organisms is well established, the expression profile and function of TLRs in various micro-environmentally differentiated regions of the GI tract has not been delineated. Altered TLR expression on intestinal epithelial cells and/or mediated signals may cause aberrant immunity, infection, inflammation and/or malignant transformation in the GI tract.

The expression levels of the five major TLRs (1, 2, 4, 6, and 10) and their adaptor protein MyD88 in a novel cellular system of adult intestinal stem cells and differentiated epithelial lineages derived from these Epi-SCs, from each segment of the intestinal tract (duodenum through rectum) has been determined.

Methods: Regional differences in TLR expression among various segments of the small and large intestine were examined by RT-PCR of RNA isolated from stem cells that have been shown to be positive for stem cell markers: Oct4, Nanog and LIN28. Both β-tubulin and GAPDH served as control genes. The Epi-SC nature of these cells was further demonstrated by the expression of markers specific to each of the four epithelial lineage subtypes present in the intestinal epithelium: chromogranin-A for enteroendocrine; MUC2 and trefoil factor 3 for goblet; sucrase isomaltase, alkaline phosphatase, and dipeptidyl-peptidase-4 for columnar; and lyzozyme, defensin, and MMPI for Paneth epithelial cells.

Results: The gram positive pathogen signaling TLRs (TLR1 and TLR6) were preferentially expressed by small intestinal and the rectal Epi-SCs. Whereas, mRNA for the Gram negative sensory TLR2 and TLR4 was detected in Epi-SCs derived from all segments (small intestine>>large intestine) of the GI tract. Interestingly, TLR10 mRNA expression was strongest in rectum and was higher overall than any other TLR. Additionally, the mRNA level for TLR adaptor protein MyD88 was comparable (with slight variations) in all cell lines.

Conclusion: These results suggested a unique expression profile of functional TLRs on epithelial stem cells derived from micro-environmentally distinct regions of the GI tract. These findings will aid in understanding the mechanisms of innate immune response and help to better devise protection against microbial invasion in the intestine and the resulting diseases.

Example 4

Expression of Toll-Like Receptors

The HIPEC lines derived from adult stem cells isolated from different gastrointestinal tract regions were analyzed for Toll-like Receptor expression. The different HIPEC lines were shown to possess different expression patterns of TLR receptors. The lower β-tubulin control amplification was done to provide a reference amplification for myD88 because it was amplified from a different oligo dT primed RT than the other PCRs.

Cell lines from the duodenum, jejunum, ileum, ascending colon, transverse colon, sigmoid, rectum, and jejunum in HIPEC-1 were cultured for 10 passages. Total RNA during selected passages of each of the cell lines was collected. These collections included the total RNA from the: (a) 1st passage of cell lines cultured from the ileum and ascending colon; (b) 2nd passage of the cell line cultured from the jejunum; (c) 4th passage of the cell line cultured from the sigmoid; (d) 6th passage of the cell lines cultured from the jejunum, ascending colon, rectum, and jejunum in HIPEC-1; (e) 7th passage of the cell line cultured from the duodenum; (f) 8th passage of the cell line cultured from the sigmoid; and (g) 9th passage of the cell line cultured from the transverse colon. This total RNA then was separately analyzed for the presence of the TLR proteins, as well as β-tubulin (positive control), utilizing RT-PCR (see FIG. 14). The TLR proteins included hTLR1, hTLR2, hTLR4, hTLR6, and hTLR10. An equal amount of initial total RNA template was used, then the amount further refined based upon the amplification of the β-tubulin positive control.

Figure 15:
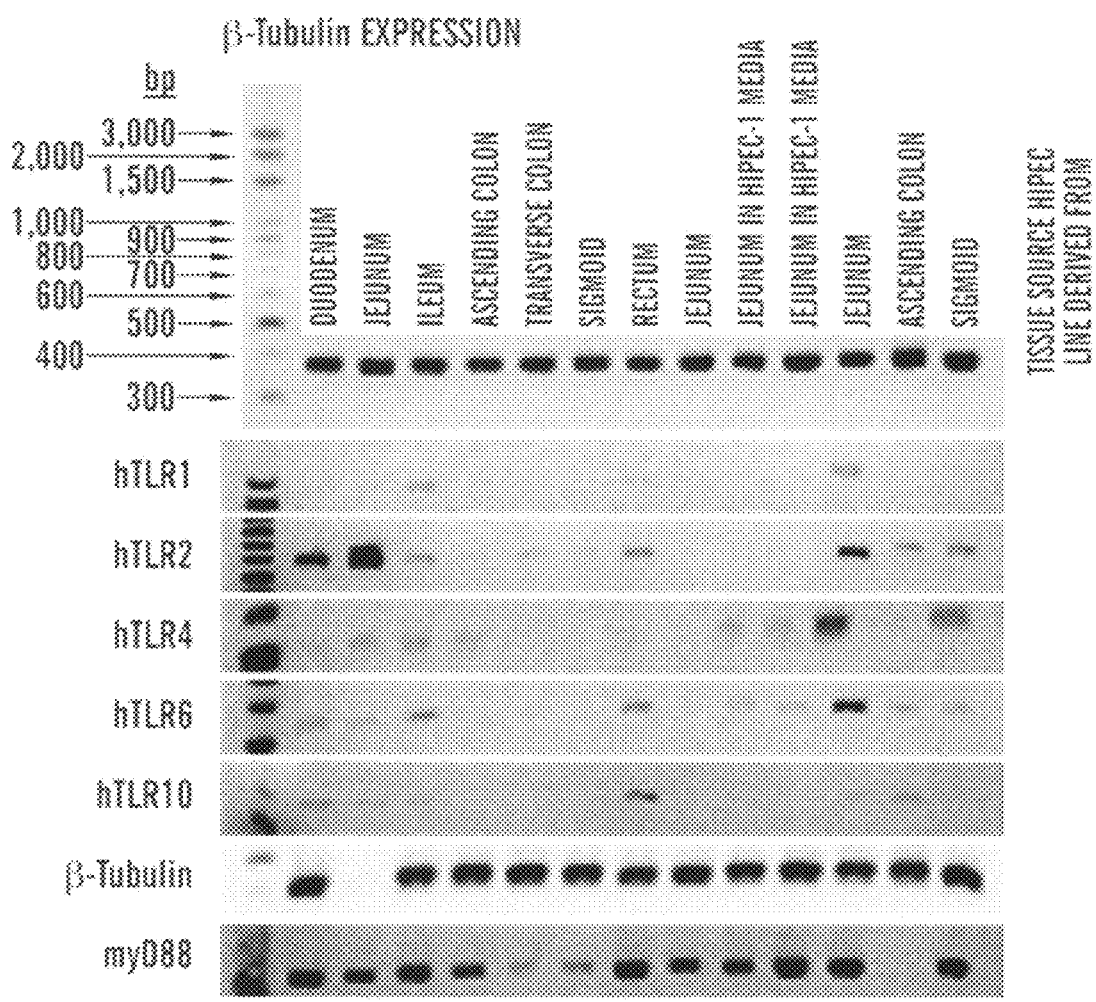
FIG. 15 shows the TLR expression pattern of various HIPEC lines derived from GI stem cell lines. RT-PCR products from total RNA preparations of non-transformed HIPEC lines derived from various ahGISC lines derived from 10 regions (i.e., segments) of the gastrointestinal tract are shown for various TLRs. Lane: (1) molecular weight marker; (2) duodenum tissue source; (3) jejunum tissue source; (4) ileum tissue source; (5) ascending colon tissue source; (6) transverse colon tissue source; (7) sigmoid tissue source; (8) rectum tissue source; (9) jejunum tissue source; (10) jejunum in HIPEC-1 media; (11) jejunum in HIPEC-1 media; (12) jejunum tissue source; (13) ascending colon tissue source; and (14) sigmoid tissue source.
Figure 16:
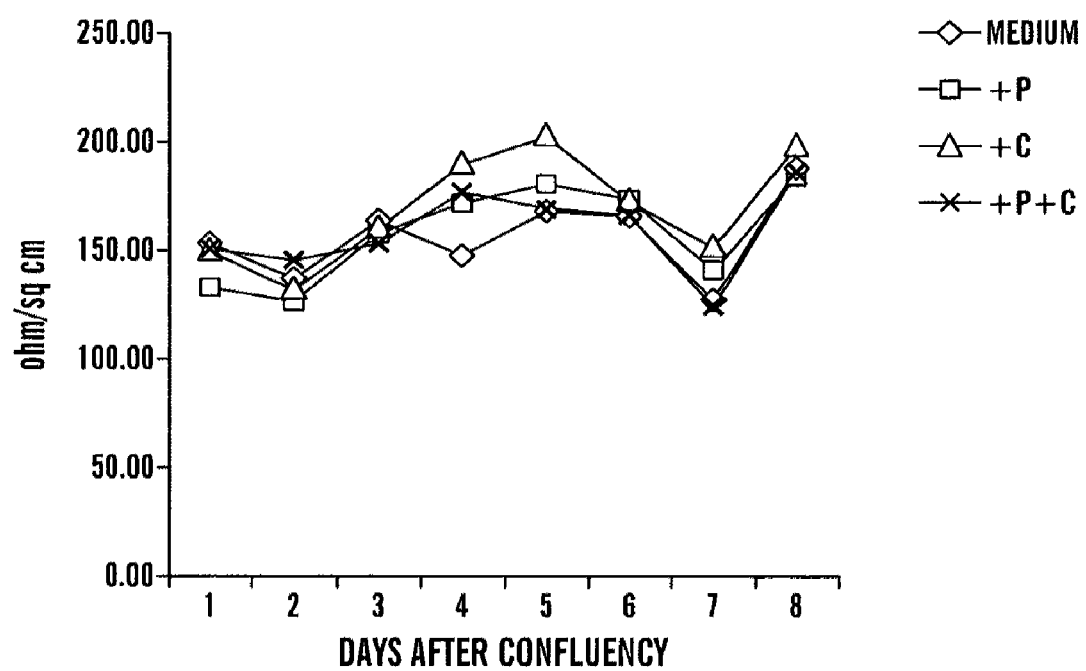
FIG. 16 is a graph showing trans-epithelial electrical resistance (TEER) of HIPEC monolayers grown on trans-well filters.
Figure 17B:
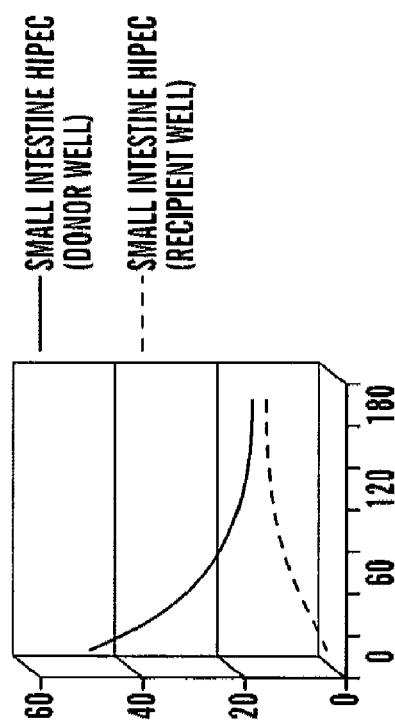
FIGS. 17A and 17B are graphs showing results from a drug (Propanolol) permeability assessment of HIPEC monolayers derived from colon (FIG. 17A) and small intestinal (FIG. 17B) segments.
Figure 17A:
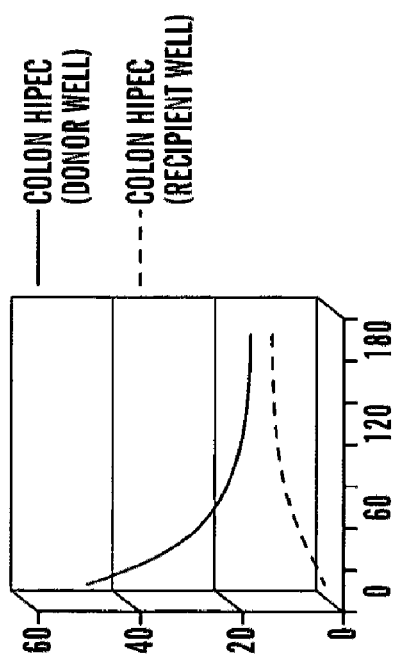

FIG. 15 shows the RT-PCR amplification products of human TLR templates derived from HIPEC lines. FIG. 15 reveals that (i) hTLR1 was expressed in the cell lines derived from the ileum, rectum and jejunum; (ii) hTLR2 was expressed in the cell lines derived from the duodenum, jejunum, ileum, ascending colon, transverse colon, sigmoid, and rectum; (iii) hTLR4 was expressed in the cell lines derived from the duodenum, jejunum, ileum, ascending colon, rectum, jejunum in HIPEC-1, jejunum and sigmoid; (iv) hTLR6 was expressed in the cell lines derived from the duodenum, jejunum, ileum, rectum, jejunum HIPEC-1, jejunum, ascending colon, and sigmoid; and (v) hTLR10 was expressed in the cell lines derived from the duodenum, jejunum, ileum, rectum, jejunum, and ascending colon. All cell lines expressed the β-tubulin positive control.

These results showed that the cell lines cultured from different segments of the gastrointestinal tract differ in their expressed TLR proteins. This data further demonstrated the retention of differentiation capability of these stem cell cultures as the cell lines exhibit differential expression of TLR at different passages.

Example 5

Activation and Repression of Differentiation: Expression of TLR-2

FIG. 15 shows RT-PCR products of a total RNA prep from cell line A2J1. The cell line demonstrated extremely low levels of TLR-2 expression when grown in HIPEC-1 media, which was reversed in HIPEC-2 media. This increased expression could be inhibited by the addition of conditioned media fraction P. The expression of TLR-2 is indicative of increased epithelial differentiation.

The activation and repression of differentiation was analyzed. Briefly, the expression of the enterocyte epithelial marker sucrase isomaltase (SI) was assayed. An electrophoresis gel was produced of the cell markers DEFA5, SI, ITGIβ1, and KRT18 from HIPEC cell lines HIPEC-2, HIPEC-2+P, HIPEC-2+C, and HIPEC-2+P+C. The gel showed the expression or enterocyte epithelial marker sucrase isomaltase (SI) is decreased in HIPEC-1 and increased in HIPEC-2. SI expression is further increased by the addition of factor C to the HIPEC-2 media.

Example 6

TLR Expression Pattern of GI Stem Cell Lines

Figure 14:
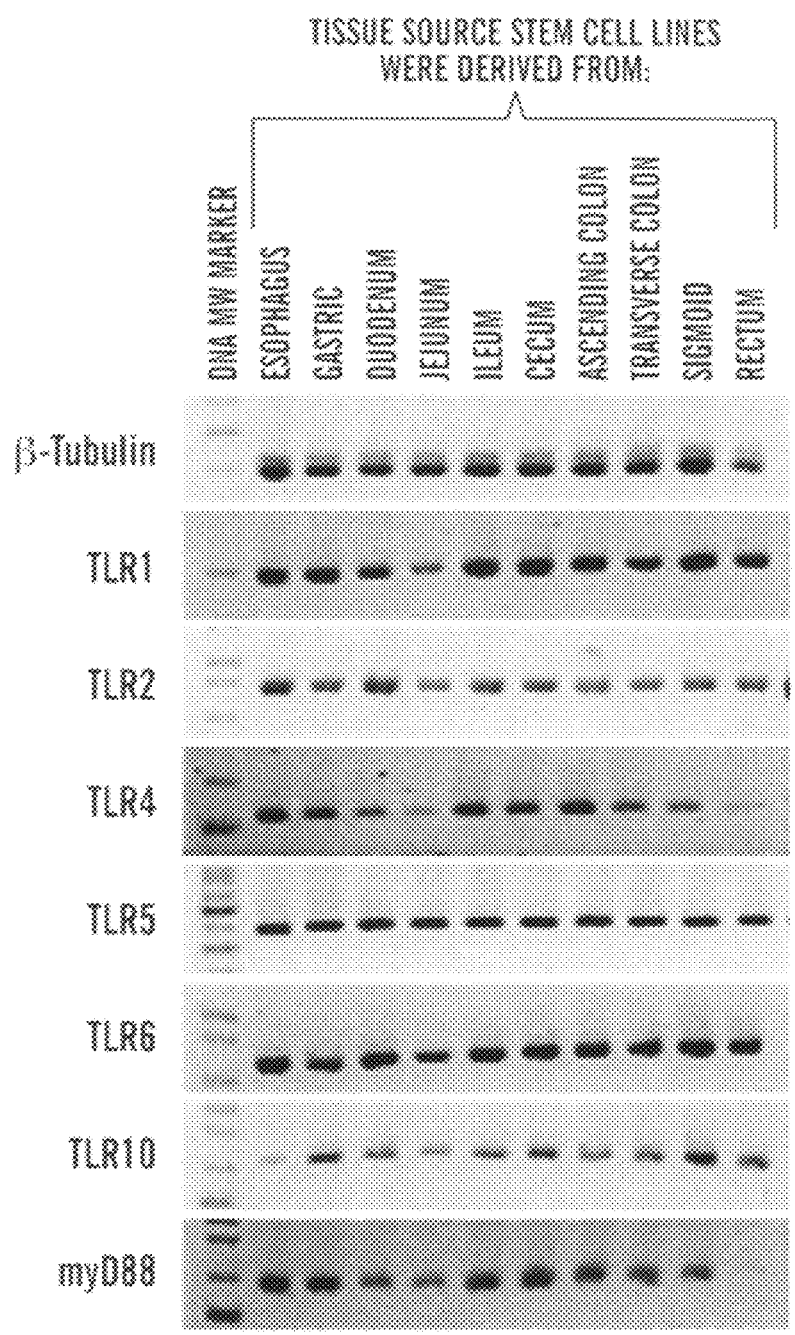
FIG. 14 shows the TLR expression pattern in GI stem cell lines. RT-PCR products from total RNA preparations of stem cell lines derived from 10 regions (i.e., segments) of the gastrointestinal tract are shown for various TLRs. Lane: (1) molecular weight marker; (2) esophogus derived stem cell line; (3) gastric derived stem cell line; (4) duodenum derived stem cell line; (5) jejunum derived stem cell line; (6) ileum derived stem cell line; (7) cecum derived stem cell line; (8) ascending colon derived stem cell line; (9) transverse colon derived stem cell line; (10) sigmoid derived stem cell line; and (11) rectum derived stem cell line.

As shown in FIG. 14, RT-PCR of total RNA was prepared from stem cell lines cultured from 10 regions/tissues of the GI tract. All lines demonstrated some variable level expression of TLR1, TLR2, TLR4, TLR5, TLR6, TLR10, and myD88. Rectal derived stem cells showed very low levels of TLR4 and myD88, where as, TLR1, TLR5, and TLR6 expression was fairly consistent in all GI tract derived stem cells lines.

Example 7

TLR Expression Pattern of HIPEC Lines Derived from GI Stem Cell Lines

As shown in FIG. 15, RT-PCR of total RNA was prepared from non-transformed human intestinal primary epithelial cell (HIPEC) lines derived from adult GI stem cell lines cultured from 10 regions/tissues of the GI tract. The gram positive pathogen signaling TLRs (TLR1 and TLR6) were preferentially expressed by small intestinal and the rectal Epi-SCs. Whereas, mRNA for the Gram negative sensory TLR2 and TLR4 was detected in Epi-SCs derived from all segments (small intestine>>large intestine) of the GI tract. Interestingly, TLR10 mRNA expression was strongest in rectum and was higher overall than any other TLR. Additionally, the mRNA level for TLR adaptor protein MyD88 was comparable (with slight variations) in all cell lines. Unlike the stem cell data depicted above, these cells lines were derived from multiple individuals, therefore, the observed variable levels of expression may represent normal variation between individuals. Further whole GI tract analysis will answer this question.

Example 8

Nitric Oxide Regulation by HIPEC Lines in Response to Immunostimulation

Nitric oxide (NO) is a short-life molecule produced by the enzyme known as the nitric oxide synthase (NOS), in a reaction that converts arginine and oxygen into citrulline and NO. There are three isoforms of the enzyme: neuronal NOS (nNOS, also called NOS1), inducible NOS (iNOS or NOS2), and endothelial NOS (eNOS or NOS3). It is now known that each of these isoforms may be expressed in a variety of tissues and cell types. Various functions of NO have been known to play critical roles in pathophysiology of chronic inflammatory and malignant diseases such as, asthma, chronic liver diseases, inflammatory bowel disease (IBD), arthritis, cancer, cardiovascular diseases, diseases of central nervous system (CNS), etc. The ubiquitous role that the simple gas nitric oxide plays in the body, from maintaining vascular homeostasis and fighting infections to acting as a neurotransmitter and its role in cancer, has spurred a lot of interest among researchers all over the world. Nitric oxide plays an important role in the physiologic modulation of coronary artery tone and myocardial function. Nitric oxide from iNOS appears to be a key mediator of such glial-induced neuronal death. The high sensitivity of neurons to NO is partly due to NO causing inhibition of respiration, rapid glutamate release from both astrocytes and neurons, and subsequent excitotoxic death of the neurons.

Gastrointestinal (GI) inflammation is a global health burden. Yet the mechanism of GI inflammation remains undefined. Among proposed mechanisms, increased nitric oxide (NO) production by intestinal epithelial cells (EC) is thought to play a crucial role in inflammatory conditions such as IBD. However, the regulation of NO production in human intestinal epithelium are undefined, thus treatments for these diseases remain inadequate.

Figure 18:
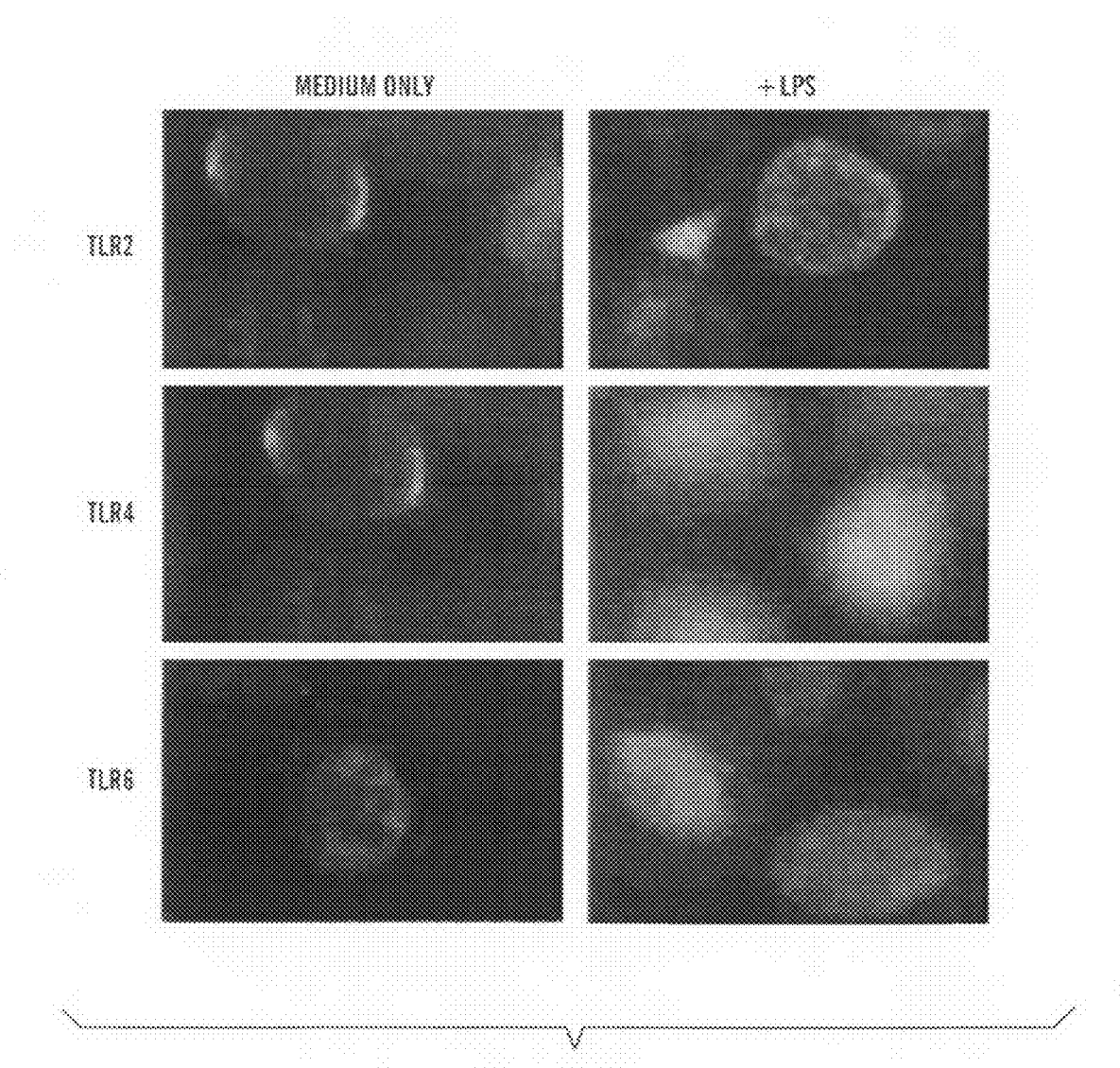
FIG. 18 shows assay results of regulation of TLR expression by lipopolysaccharide (LPS) on an hGISC-derived primary epithelial cell line. Results show that LPS stimulation upregulated expression of all three TLRs tested (i.e., TLR2, TLR4, and TLR6).

A preliminary experiment confirmed that lipopolysaccharide (LPS), a known immunostimulatory agent, upregulated expression in an HIPEC line of the present invention of all three TLRs tested (i.e., TLR2, TLR4, and TLR6) (see FIG. 18).

Figure 19:
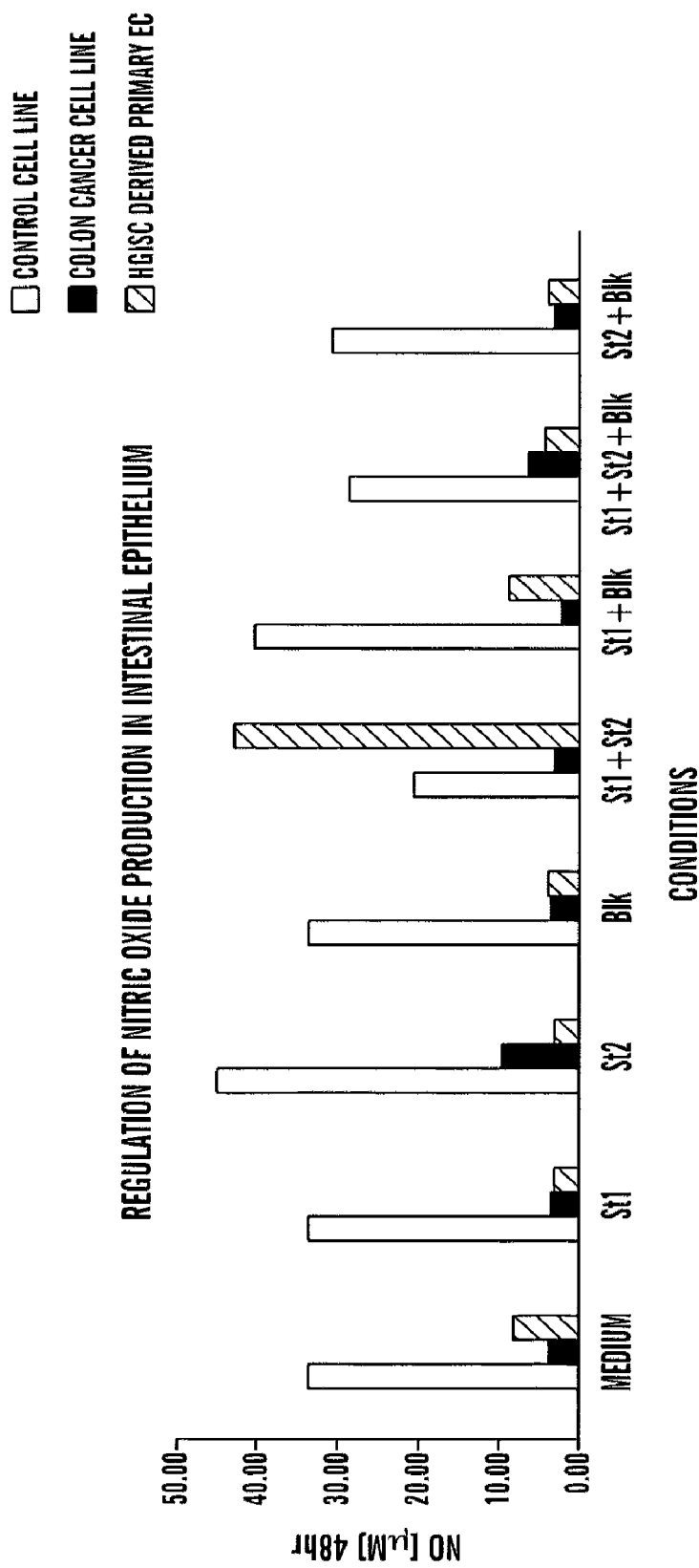
FIG. 19 is a graph showing regulation of nitric oxide (NO) production in intestinal epithelim. Control cell line (blue), Colon Cancer cell line (red), and hGISC derived primary epithelial cell line (green). St1=LPS. St2=IFN-γ. Blk=LNMMA.
Figure 20:
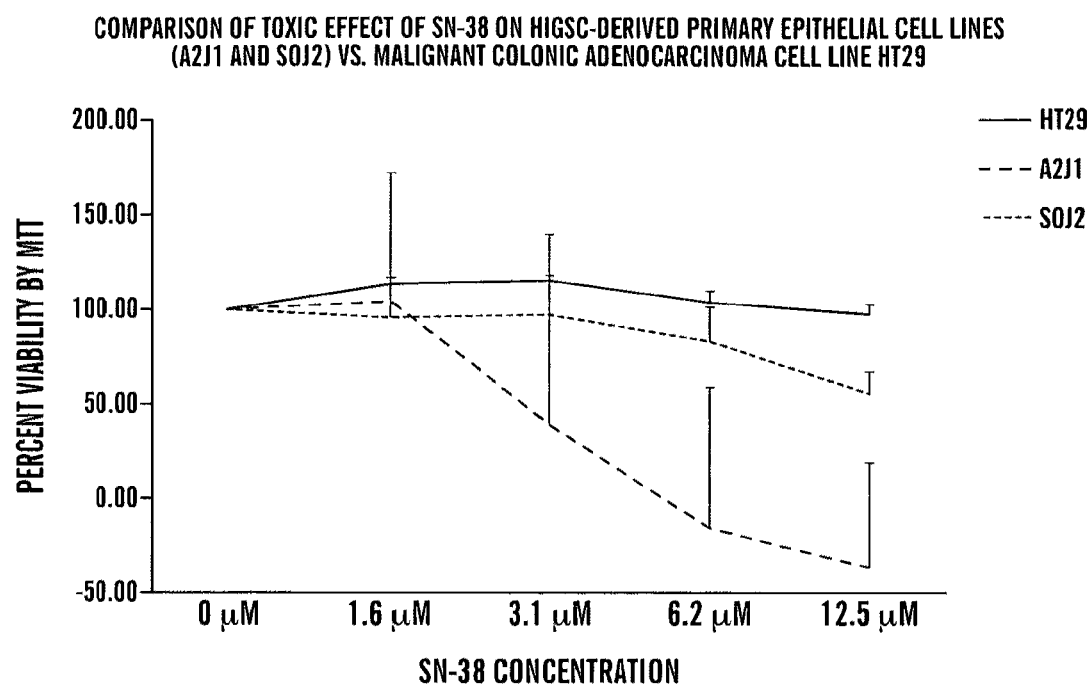
FIG. 20 is a graph showing the percent viability of the cultures as determined by MTT plotted against SN-38 concentration. A2J1 and 50J2 are hGISC-derived primary epithelial cell lines. HT29 is a malignant colonic adenocarcinoma.

Therefore, to gain insight about NO production regulation by intestinal EC, the effects of innate (LPS) and adaptive (IFN-γ) immunostimulatory agents on embodiments of the hGISC cell system derived non-transformed primary epithelial cells (EC) were studied and compared to a colonic adenocarcinoma EC line HT29. It was found that human gastrointestinal stem cell (hGISC) derived non-transformed epithelial cells but not malignant colonic adenocarcinoma cell line HT29 respond to combined innate and adaptive immunostimulation by producing high levels of nitric oxide (see FIG. 19).

Assays to determine the regulation of nitric oxide production by hGISC derived HIPECs stimulated with various pathogen associated molecular patterns (PAMPs) involved the following: Non-transformed epithelial cells ($2 \times 10^4$) were cultured in the presence or absence of LPS (1 μg/ml), IFN-γ (100 u/ml) in phenol-red-free DMEM medium in 96 well tissue culture plate in duplicates for 48 hours. Cell free culture supernatants were collected and analyzed for NO content using a Griess Reaction kit (e.g., Griess Reagent System, Part #TB229) (PROMEGA, Madison, Wis.) in accordance with the manufacturer's instructions.

In another assay for NO, a macrophage cell line MHS served as a positive control. Cells were cultured with/without LPS (1 μm/ml), IFN-γ (200 u/ml), or in combination for 24 hours. Culture supernatants were analyzed for NO content by Griess reaction assay (as mentioned herein). Results showed that neither LPS nor IFN-γ alone affect NO production by intestinal ECs. However, NO production by hGISC derived primary ECs was dramatically increased (comparable to the NO level seen in MHS cells) when LPS and IFN-y were added in combination. In contrast, malignant HT29 cells did not show any difference in NO synthesis even when LPS (innate stimuli) and IFN-γ (adaptive stimuli) were combined.

These findings assist in understanding the intestinal inflammatory disease mechanisms and development of new treatments.

Example 9

Assessment of the Intestinal Primary Epithelial Cell System

Embodiments of the intestinal primary epithelial cell system of the present invention were analyzed and characterized for various cell functions.

An embodiment of an HIPEC line of the present invention was tested for gross morphology and compared with the morphology of a Caco-2 cell line. The HIPEC line tested was shown to have cells that grow well and have epithelial-like morphology. There was no evidence of senenscence after more than 6 weeks (>16 passages).

Using qPCR, the HIPEC line was also tested for various markers for mature phenotype cells, including the following cell subtypes: enteroendocrine; Goblet; Paneth; and enterocyte. The following markers were used, with the corresponding cell subtypes in parentheses: Somatostatin (enteroendocrine); Glucagon (enteroendocrine); Lysozyme (Goblet/Paneth); Defensin 5 (Goblet/Paneth); Trefoil factor 3 (Goblet/Paneth); Mucin 2 (Goblet/Paneth); Sucrose isomaltase (enterocyte); Carbonic anhydrase (enterocyte); Cd×2 promoter (enterocyte); and Guanylate cyclase c (enterocyte). Data from these tests supported a Goblet/secretory differentiation profile for the HIPEC line identified as A2J1 (derived from jejunem tissue). Data also showed no change in phenotype upon stimulation with 1 ng/ml IL-1b or 25 ng/ml TNFα (24 hrs).

Using qPCR, HIPEC lines (designated as A5A and A2J1) were tested for TLR expression. Expression of TLR2, TLR4, TLR5, and 18S ribosomal RNA was tested. Other cells tested for TLR expression included HT29, Caco2 (flask), Caco2 (filters), human colon, and controls. TLR expression was observed in the HIPEC lines of the present invention.

Using both IL-8 and MIP-3α read-out procedures, an HIPEC line of the present invention (A2J1) was tested for response to various inflammatory mediators (stimulators). The HIPEC line was compared to a Caco-2 cell line. The following stimulators were used at various concentrations: IL-1β; TNFα; IFNγ; Pam3CSK4 (TLR2); LPS (TLR4); and Flagellin (TLR5).

In conclusion, based on the tests described in this example, the HIPEC line (A2J1) was shown to have intestinal epithelial cell morphology and express some Goblet cell/secretory cell markers. A2J1 was shown to express TLR4 and TLR5, but not TLR2, which is similar to some intestinal epithelial tumor cell lines. A2J1 was responsive to IL-1β, TNFα, IFNγ, TLR5 stimulation (IL-8 response), and low level expression of MIP-3α (CCL20; anti-microbial/chemokine).

Example 10

Inulin Permeability Through Intestinal Stem Cell Derived Primary Epithelial Cell Monolayers Intestinal stem cell derived primary epithelial cell mono layers were tested for Inulin permeability.

Confluent monolayers of HIPEC cells were grown on transwell membranes in triplicates. Cells were then treated with or without pro-inflammatory cytokines for 24 hrs. $^3$H-labeled Inulin was added to the upper chamber. Aliquots of medium retrieved from the upper and lower chambers were counted.

The % amount of inulin activity transported from the upper to the lower chamber was determined. The results are shown in Table 5 below, along with the standard error.

TABLE 5

Inulin Permeability of HIPEC Monolayers Grown on TransWell Filters

| Conditions | Experiment #1 | Experiment #2 | Experiment #3 |
|---|---|---|---|
| Medium Only | 35.5% +/− 5.3 | 41.6% +/− 0.96 | 43.6% +/− 1.16 |
| +IL-1α | 40.0% +/− 3.6 | 47.4% +/− 0.59 | 50.7% +/− 0.40 |
| +IL-1β | 43.5% +/− 1.36 | 50.4% +/− 0.94 | 54.0% +/− 1.59 |
| +TNF-α | 41.2% +/− 0.66 | 46.6% +/− 1.05 | 49.0% +/− 1.95 |

TABLE 5-continued

Inulin Permeability of HIPEC Monolayers
Grown on TransWell Filters

| Conditions | Experiment #1 | Experiment #2 | Experiment #3 |
|---|---|---|---|
| +IFN-γ | 36.0% +/− 2.8 | 42.6% +/− 2.07 | 42.7% +/− 0.30 |
| +IL-6 | 36.5% +/− 0.48 | 41.8% +/− 0.59 | 43.1 +/− +/− 1.07 |

The results provide functional proof of tight junction formation in the HIPEC monolayer, as well as, proof of utility in permeability studies in inflammatory GI conditions.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of detecting segment-specific activation or suppression of a Toll-like receptor (TLR) in an epithelial cell system in response to a target agent, said method comprising:
providing an intestinal primary epithelial cell system for detecting gastrointestinal segment-specific activation or suppression of a Toll-like receptor (TLR) by a target agent, said system comprising an isolated human intestinal primary epithelial cell (HIPEC) line that expresses in a segment-specific manner at least one TLR selected from the group consisting of TLR1, TLR2, TLR3, TLR4, TLR5, TLR6, TLR7, TLR8, TLR9, TLR10, TLR11, TLR12, and TLR13, wherein said HIPEC line is derived from a differentiable adult human gastrointestinal stem cell (ahGISC) line derived from at least one human gastrointestinal segment selected from the group consisting of an esophagus segment, a stomach segment, a jejunum segment, an ileum segment, a duodenum segment, a cecum segment, an appendix segment, an ascending colon segment, a transverse colon segment, a descending colon segment, a sigmoid colon segment, and a rectum segment;
contacting the cell system with a target agent; and
subjecting the cell system to a TLR expression assay to determine a TLR expression profile of the cell system in response to the target agent, thereby determining whether the target agent activates, suppresses, or has no effect on TLR expression in the cell system.

2. The method according to claim 1, wherein the TLR expression assay is effective to determine whether the cell system's response to the target agent is due to a direct or indirect interaction between the target agent and TLR.

3. The method according to claim 1, wherein the target agent binds to at least one TLR, is an activator of at least one TLR, is an enhancer of at least one TLR, inhibits at least one TLR, is an agonist of at least one TLR, or is an antagonist of at least one TLR.

4. The method according to claim 1, wherein the target agent is a therapeutic agent for treating a disorder that alters TLR expression on intestinal epithelial cells and/or mediated signals, said disorder being selected from the group consisting of autoimmunity disorders, bacterial infections, viral infections, parasite infections, protozoan infections, fungal infections, fungal-associated disorders, basal cell carcinoma, herpes simplex virus (HSV-1), encephalitis (HSE), and human primary immunodeficiency.

5. The method according to claim 1, wherein the target agent is an immunostimulatory agent.

6. The method according to claim 1, wherein the target agent comprises a human pathogen or is derived from a human pathogen, said human pathogen being selected from the group consisting of a virus, a bacterium, a fungus, a parasite, and a protozoan.

7. The method according to claim 6, wherein the target agent derived from a human pathogen is a type of agent selected from the group consisting of a compound, a nucleic acid molecule, a peptide, an enzyme, a biomarker, a toxin, and the like.

8. The method according to claim 1, wherein the target agent is subject to screening for use as a therapeutic effective to a treat gastrointestinal disorder.

9. The method according to claim 8, wherein the gastrointestinal disorder is selected from the group consisting of achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis.

10. The method according to claim 1, wherein the HIPEC line has a TLR expression profile that corresponds to a particular mature cell phenotype, wherein said mature cell phenotype is selected from the group consisting of a columnar epithelial cell, a Paneth cell, a Goblet cell, an enteroendocrine chromaffin cell, a neuronal cell type, and a mesenchymal cell.

11. The method according to claim 1, wherein the HIPEC line comprises cells having a mature cell phenotype selected from the group consisting of a columnar epithelial cell, a Paneth cell, a Goblet cell, an enteroendocrine chromaffin cell, a neuronal cell type, and a mesenchymal cell.

12. The method according to claim 1, wherein the ahGISC line comprises cells expressing at least one stem cell biomarker selected from the group consisting of Nanog, LIN28, Oct4, SOX2, Bmi-1, and Lgr5.

13. The method according to claim 1, wherein the ahGISC line comprises cells having at least a β-1-integrin$^{(+)}$cytokeratin$^{(+)}$phenotype.

14. The method according to claim 1, wherein the ahGISC line comprises cells having a phenotype of cytokeratin(+), β-intergrin(+), defensin-5(+), trefoil factor-3(+), mucin-2(+), chomogranin-A(+), intestinal alkaline phosphatase(+), lysozyme(+).

15. The method according to claim 1, wherein the subjecting step further comprises:
determining segmental bioavailability of the target agent.

16. The method according to claim 1, wherein the cell system is provided in the form of a cell monolayer.

17. The method according to claim 5, wherein the immunostimulatory agent is selected from the group consisting of lipopolysaccharide (LPS), an interferon (IFN) such as IFN-α, IFN-β, IFN-γ, and IFN-ω, an interleukin (IL) such IL-1β, IL-8, and IL-18, a cytokine such as tumor necrosis factor alpha (TNFα), a synthetic lipoprotein such as Pam3CSK4, Flagellin, and the like.

18. The method according to claim 8, wherein the subjecting step further comprises:
determining whether the gastrointestinal disorder develops by way of a TLR-mediated mechanism in a gastrointestinal segment-specific manner.

* * * * *

SEQUENCE LISTING

<160> NUMBER OF SEQ ID NOS: 34

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
atgcctgtga tttgtgggcc                                         20

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
caaccagcag tttgcaggtg gctg                                    24

<210> SEQ ID NO 3
<211> LENGTH: 25
<212> TYPE: DNA
<213> ORGANISM: Artificial
<220> FEATURE:
<223> OTHER INFORMATION: Primer

<400> SEQUENCE: 3
catcaaagct ctgcagaaag aactc                                   25

<210> SEQ ID NO 4
<211> LENGTH: 24
<212> TYPE: DNA
<213> ORGANISM: Artificial
<220> FEATURE:
<223> OTHER INFORMATION: Primer

<400> SEQUENCE: 4
cgggacacct ggcttcggat ttcg                                    24

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
catgagtcag tgaacaggga atg                                     23

```
<210> SEQ ID NO 6
<211> LENGTH: 28
<212> TYPE: DNA
<213> ORGANISM: Artificial
<220> FEATURE:
<223> OTHER INFORMATION: Primer

<400> SEQUENCE: 6
caaaagtctt taccaataat atttagag                                          28

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
taaaagttct agtggtacgg taggag                                            26

<210> SEQ ID NO 8
<211> LENGTH: 27
<212> TYPE: DNA
<213> ORGANISM: Artificial
<220> FEATURE:
<223> OTHER INFORMATION: Primer

<400> SEQUENCE: 8
cataatagaa tgtctacatt ccttctg                                           27

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
gatctgtctt acaacctatt agaag                                             25

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
ctgaaaacac atgtagataa tggc                                              24

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
gttcttggac taaaagttta ttaag                                             25

<210> SEQ ID NO 12
<211> LENGTH: 24
<212> TYPE: DNA
<213> ORGANISM: Artificial
<220> FEATURE:
<223> OTHER INFORMATION: Primer
```

```
<400> SEQUENCE: 12
cttatccagc acacgaatac acag                                          24

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
tggatacgtt tccttataag                                               20

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
ttggactcat atcaagatgc tctg                                          24

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15
atgcttttcc cgaattatcc tacg                                          24

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
ctccaggacc gcccgccatg gctg                                          24

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
ctgtgtgtaa acatgacttc caag                                          24

<210> SEQ ID NO 18
<211> LENGTH: 25
<212> TYPE: DNA
<213> ORGANISM: Artificial
<220> FEATURE:
<223> OTHER INFORMATION: Primer

<400> SEQUENCE: 18
ctcatcttca cacgtcttca ggttg                                         25

<210> SEQ ID NO 19
<211> LENGTH: 26
<212> TYPE: DNA
```

```
<213> ORGANISM: Artificial
<220> FEATURE:
<223> OTHER INFORMATION: Primer

<400> SEQUENCE: 19
gaaccctcac ttgcatttgg acagag                                          26

<210> SEQ ID NO 20
<211> LENGTH: 25
<212> TYPE: DNA
<213> ORGANISM: Artificial
<220> FEATURE:
<223> OTHER INFORMATION: Primer

<400> SEQUENCE: 20
ctgcttgatc gcttgccctt ctggc                                           25

<210> SEQ ID NO 21
<211> LENGTH: 24
<212> TYPE: DNA
<213> ORGANISM: Artificial
<220> FEATURE:
<223> OTHER INFORMATION: Primer

<400> SEQUENCE: 21
cttgtaagaa cataaacaca ccag                                            24

<210> SEQ ID NO 22
<211> LENGTH: 24
<212> TYPE: DNA
<213> ORGANISM: Artificial
<220> FEATURE:
<223> OTHER INFORMATION: Primer

<400> SEQUENCE: 22
ggtttctgct ttgcatatct cctg                                            24

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
gccgaatctt ttaaaataca actacg                                          26

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
ggaagtggac cattccttct ccag                                            24

<210> SEQ ID NO 25
<211> LENGTH: 25
<212> TYPE: DNA
<213> ORGANISM: Artificial
<220> FEATURE:
<223> OTHER INFORMATION: Primer

<400> SEQUENCE: 25
cttcaaggtc acgttcatct tgagc                                           25
```

```
<210> SEQ ID NO 26
<211> LENGTH: 24
<212> TYPE: DNA
<213> ORGANISM: Artificial
<220> FEATURE:
<223> OTHER INFORMATION: Primer

<400> SEQUENCE: 26
ctggaggctt agggaccaag gctg                                              24

<210> SEQ ID NO 27
<211> LENGTH: 25
<212> TYPE: DNA
<213> ORGANISM: Artificial
<220> FEATURE:
<223> OTHER INFORMATION: Primer

<400> SEQUENCE: 27
gtgataactg ctaggaatgg agtac                                             25

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
ttgaagttct ccagctcctg                                                   20

<210> SEQ ID NO 29
<211> LENGTH: 19
<212> TYPE: DNA
<213> ORGANISM: Artificial
<220> FEATURE:
<223> OTHER INFORMATION: Primer

<400> SEQUENCE: 29
gaaatggagg caccccttc                                                    19

<210> SEQ ID NO 30
<211> LENGTH: 25
<212> TYPE: DNA
<213> ORGANISM: Artificial
<220> FEATURE:
<223> OTHER INFORMATION: Primer

<400> SEQUENCE: 30
tcagaatttg tagactttct gtctc                                             25

<210> SEQ ID NO 31
<211> LENGTH: 24
<212> TYPE: DNA
<213> ORGANISM: Artificial
<220> FEATURE:
<223> OTHER INFORMATION: Primer

<400> SEQUENCE: 31
caaccatcat gacctctgaa tatg                                              24

<210> SEQ ID NO 32
<211> LENGTH: 25
<212> TYPE: DNA
<213> ORGANISM: Artificial
<220> FEATURE:
<223> OTHER INFORMATION: Primer
```

-continued

```
<400> SEQUENCE: 32
gttccagttg ccggatcatc tcctg                                          25

<210> SEQ ID NO 33
<211> LENGTH: 27
<212> TYPE: DNA
<213> ORGANISM: Artificial
<220> FEATURE:
<223> OTHER INFORMATION: Primer

<400> SEQUENCE: 33
gaattttttt atgaattctc agccctc                                        27

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
tttttttttt tttttttttt                                                20
```